US006779468B1

(12) United States Patent
Gupta

(10) Patent No.: US 6,779,468 B1
(45) Date of Patent: Aug. 24, 2004

(54) METHOD AND PHARMACEUTICAL COMPOSITION FOR IRON DELIVERY IN HEMODIALYSIS AND PERITONEAL DIALYSIS PATIENTS

(76) Inventor: Ajay Gupta, 39151 Horton, Farmington Hills, MI (US) 48331

( * ) Notice: Subject to any disclaimer, the term of this patent is extended or adjusted under 35 U.S.C. 154(b) by 0 days.

(21) Appl. No.: 09/341,032

(22) PCT Filed: Dec. 30, 1997

(86) PCT No.: PCT/US97/23719

§ 371 (c)(1),
(2), (4) Date: Sep. 8, 1999

(87) PCT Pub. No.: WO98/29434

PCT Pub. Date: Jul. 9, 1998

Related U.S. Application Data

(60) Provisional application No. 60/055,315, filed on Aug. 7, 1997.

(51) Int. Cl.⁷ .............................................. B01D 11/00
(52) U.S. Cl. ....................... 110/647; 210/646; 424/603; 424/646; 424/647
(58) Field of Search .................................. 424/603, 646, 424/647; 210/646, 647

(56) References Cited

U.S. PATENT DOCUMENTS

| 3,911,915 A | 10/1975 | Seifter et al. ................ 424/180 |
| 4,315,942 A | 2/1982 | Corden ........................ 424/295 |
| 4,756,838 A | 7/1988 | Veltman ........................ 252/1 |
| 5,108,767 A | 4/1992 | Mulchandani et al. ......... 426/72 |
| 5,393,777 A | 2/1995 | Crosa ......................... 514/502 |
| 5,906,978 A | 5/1999 | Ash ............................ 514/23 |

OTHER PUBLICATIONS

Tsuji, 4 et al. Eur. J. Surg. 161: 29–33, 1995.*
Provisional Pat. application Ser. No. 60/023,926, filed Aug. 14, 1996.
Sunder–Plassmann et al., *Nephrol Dial Transplant*, 11:1797–1802 (1996).
Rubinger et al., *Amer. J. Kidney Diseases*, VII No. 2:125–129 (1986).
Zanen et al., *Neprol Dial Transplant*, 11:820–824 (1996).
*The Merck Index*, Merck and Co., Inc., Rahway, NJ, Budaveri Ed., 11th Edidtion:3969 (1989).
*Dorland's Illustrated Medical Dictionary*, WB Saunders Co., 27th Edition:462, 741, 837, 1541 (1985).
Berner et al., *J. Nutr.*, 115:1042–1049 (1985).
Hazell et al., *Br. J. Nutr.*, 39:631–639 (1978).
Basta, et al., Iron deficiency anemia and the productivity of adult males in Indonesia, *Am. J. Clin. Nutr.*, 32:916 (1979).
Brown et al., Intravenously administered saccharated iron oxide in the treatment of hypochromic anemia, *JAMA*, 144:1084–1089 (1950).

Calver et al., Intravenous administration of iron gluconate during hemodialysis, *Iron Research*, New York:Plenum Press, 1994:219–228.
Cook et al., Iron deficiency: The global perspective, In.:Hershko, C. Ed. Progress in Iron Research, New York: Plenum Press, 1994:219–228.
Fishbane et al., The safety of intravenous iron dextran in Hemodialysis Patients, *Am. J. Kidney Dis.*, 28:529–534 (1996).
Lieberman et al., Association of maternal hematocrit with premature labor, *Am. J. Obstet. Cynecol.*, 159:107 (1988).
Lozoff et al., Long–term developmental outcome of infants with iron deficiency, *N. Engl. J. Med.*, 325:687 (1991).
NFK–DOQI clinical practical guidelines for the treatment of anemia of chronic renal failure, *Am. J. Kid. Dis.*, 30:S192–S137 (1997).
Ohira et al., Work capacity, heart rate and blood lactate responses to iron treatment, *Br. J. Haematol.*, 41:365 (1983).
Oski et al., The effects of therapy on the developmental scores of iron–deficient infants, *Pediatrics*, 71:877 (1983).
Oski et al., Effect of iron therapy on behavior performance in nonanemic, iron–deficient infants, *Pediatrics*, 71:877 (1983).
Schultink et al., Low compliance with an iron–supplementation program: a study among pregnant woman in Jakarta, Indonesia, *Am.J. Cliin. Nutr.*, 32:916 (1979).
Stockman, The treatment of chlorosis by iron and some other drugs, *Br. Med. J.*, I:881–885 (1983).
Yoshifumi Tsuji et al., Effect of recombinant human erythropoietin or anamia after gastectomy, *Eur. J. Surg.*, 161:29–33 (1995).
Shimamatsu, Experience with i.v. iron chondroitin–sulphate colloid in Japanese haemodialysis patients, *Nephrol Dial Transplant*, 13:1053 (1998).
*The National Formulary* VII, 165 (1942).
Dainippon Pharmaceutical product description for BLUTAL® Injection, 175–177 (1994).
Erslev, Drug Therjapy, *N. Engl. J. Med.*, 324 (19) : 1339–1344 (1991).
Moore et al., Incidence, causes, and treatment of iron deficiency anemia in hemodialysis patients, *J. Renal. Nutrition*, 2:105–112 (1992).

(List continued on next page.)

*Primary Examiner*—Susan Ungar
*Assistant Examiner*—Minh Tam Davis
(74) *Attorney, Agent, or Firm*—Drinker Biddle & Reath LLP

(57) ABSTRACT

A method of administering iron to dialysis patients is accomplished by infusion of a noncolloidal ferric compound, soluble in hemodialysis or peritoneal dialysis solutions, by the process of dialysis. A pharmaceutical composition is provided consisting essentially of dialysis solution including a soluble noncolloidal ferric compound, preferably ferric pyrophosphate.

4 Claims, 7 Drawing Sheets

OTHER PUBLICATIONS

Kleiner et al., The role of iron and other factors in patients unresponsive to erytropoietin therapy, *Seminars in Dialysis*, 8:(1) :29–34 (1995).

Konopka et al., Iron transfer from transferrin ot ferritin mediated by polyphosphate compounds, *Biochem. Biophys. Acta.*, 677:417–423 (1981).

Konopka et al., Iron transfer from transferrin ot ferritin mediated by polyphosphate compounds, *Biochem. Biophys. Acta.*, 96(3):1408–1413 (1980).

Morgan, Iron exchange between transferrin molecules mediated by phosphate compounds and other cell metabolites, *Biochem. Biophys. Acta.*, 499(1):169–177 (1977).

Kolf, First clinical experience with artificial kidney, *Ann. Intern. Med.*, 62:608 (1965).

Scribner et al., The treatment of chronic uremia by means of intermittent hemodialysis; a preliminary report, *Trans. Amer. Soc. Artif. Int. Organs.*, 6:114 (1960).

Jacobs et al., Isolation and characterization of genomic and cDNA clones of human erythropoietin, *Nature*, 313:806–810 (1985).

Levin, The impact of epoetin alfa: quality of life and hematocrit level, *Am. J. Kid. Dis.*, XX (Su; ; 1. 1 (Jul.) : 16–20 (1992).

Eschbach et al., Iron balance in hemodialysis patients, *Ann. Intern. Med.*, 87:710–713 (1977).

Woorwood, *Blood Rev.*, 4:259–269 (1980).

Macdougall et al., Detection of functional iron deficiency during erythropoietin treatment: a new approach, *Br. Med. J.*, 304:225–226 (1992).

Van Wyck et al., Iron status in patients reciving erythropoietin for dialysis–associated anemia, *Kidney Int.*, 35:712–716 (1989).

Wingard et al., Efficacy of oral iron therapy inpatients receiving re–combinant human erythropoietin, *Am. J. Kid. Dis.*, 25:433–439 (1995).

MacDougall et al., Poor response to the treatment of renal anaemia with erythropoeitin corrected iron . . . , *Br. Med. J.*, 299:157–158 (1989).

Shcaeffer and Schaefer, The hypochromic red cell: a new parameter for monitoring or iron supplementation, *J. Perinat. Med.*, 23:83–88 (1995).

Horl, How to diagnose and correct iron deficiency during r–huEPO therapy–a consensus report, *Nephrol. Dial. Transplant.*, 11:246–250 (1996).

Sepandj et al., Econommic appraisal of maintenance parenteral iron administration in treatment of anaemia in chronic . . . , *Nephrol. Dial. Transplant.*, 11:319–322 (1996).

Rosenlof et al., Iron availability is transiently improved by intravenous iron medication in patients . . , *Clin. Nephrol.*, 43:249–255 (1995).

Fishbane and Lynn, The utility of zinc protoporphyrin for predicitng the need for intravenous iron therapy . . . , *Am. J. Kidney Dis.*, 25:426–432 (1995).

Macdougall et al., A. randomized controlled study of iron supplementation in patients treated with erythropoietin, *J. Amer. Soc. Nephrol.*, 4:428 (abstract) (1993).

Sunder–Plassmann and Horl., Imrotance of iron supply for erythropoietin therapy, *Nephrol. Dial. Transplant.*, 10:2070–2076 (1995).

Schaeffer and Schaeffer, Management of iron substitution therapy during r–HuEPO therapy in chronic renal failure patients, *Erythropoiesis*, 3:71–75 (1992).

Nyvad et al., Intravenous iron–sucrose complex to reduce epoetin demand in dialysis patients, *Lancet*, 344:1305–1306 (1994).

Hamstra et al., Intravenous iron dextran in clinical medicine, *JAMA*, 243:1726–1731 (1980).

Kumpf and Holland, Parenteral iron dextran therapy, *DICP Ann Pharmacother*, 24:162–166 (1990).

Weinberg, Iron withholding: a defense against infection and neoplasia, *Physiol. Rev.*, 64–65–102 (1984).

Heath et al., Quantitative aspects of iron deficiency in hypochromic anemia, *J. Clin. Invest.*, 11:1293 (1932).

Best and Taylor, *The Physiological Basis of Medical Practice*, The Williams & Wilkins Co., Baltimore, MD pp. 94–99 (1943).

Nissim, Intravenous administration of iron, *Lancet*, 2:49–51 (1947).

Goetsch et al., Observations on the effect of massive doses of iron given intravenously to patients with hypochromic anemia (1946).

Cox et al., Valency investigations of iron dextran ('Imferon'), *Nature*, 207:1202–1203 (1965).

Hatton et al., Removal of iron dextran by hemodialysis: as in vitro study, *Am. J. Kid. Dis.*, 26(2):327–330 (1995).

Pascual et al., Intravenous Fe–Gluconate–Na for iron–deficient patients on hemodialysis, *Nephron*, 60:121 (1992).

Allegra et al., Iron deficiency in maintenance hemodialysis patients: assessment of diagnosis criteria . . , *Nephron*, 57:175–182 (1991).

Pollack and Weaver, Guinea pig and human red cell hemolysates release iron from transferrin, *J. Lab. Clin. Med.*, 105(5) : 629–634 (1985).

Pollack et al., Iron removal from transferrin. An experimental study., *Biochim. Biophys. Acta.*, 497 (2) :487 (1977).

Morgan, Studies on the mechanism of iron release from transferrin *Biochim. Biophys. Acta.*, 580 (2) :312–326 (1979).

Carver and Frieden, Factors affecting the adenosine triphosphate in–duced release of iron from transferrin, *Biochemistry*, 17(1) :167–172 (1978).

Nilsen and Romslo, Phrophosphate as a ligand for delivery of iron to isolated rat–liver mitochondria, *Biochim. Biohys. Acta.*, 766 (1) :233–239 (1984).

Javiad et al., Interactions between infections, malnutrition and Iron nutritional status in Pakistani infants . . . , *Acta. Paeditricia Scandinavica —Supplement*, 374:141–50 (1991).

Byrd and Horwitz, Lactoferrin inhibits or promotes Legionella pneumopilla intracellular multiplication . . . , *J. Clin. Invest.*, 88 (4) :1103–1112 (1991).

Ristroph et al., Chemically defined medium for Legionella pneumphila growth, *J. Clin. Microbiology*, 13(1) :115–119 (1981).

Feeley et al., Primary isolation media for Legionnaries disease bacterium, *Journal of Clinical Microbiology*, 8(3) : 320–5 (1978).

Maurer et al., Paramagnetic pyrophosphate. Preliminary studies on magnetic resonance contrast enhancement of acute myocardial . . . , *Investigatative Radiology*, 25(2) : 153–63 (1990).

Stevenson et al., The toxicicty of Sn–pyrophosphate: clinical manifestations prior to acute LD50, *J. Nucl. Med.*, 15:252–256 (1974).

Harken et al., Early ischemica after complete coronary ligation in the rabbit, dog, pig and monkey, *Am. J. Physiol.*, 241:H202 (1981).

Kornberg, On the metabolic significance of phosphorolytic and pyrophosphorolytic reactions, In Kasha M, Pullman B, eds. *Horizons on Biochemistry*, New York, Academic Press, pp. 251–264 (1962).

Jung et al., The fate of intravenously injected 32–p–pyrophosphate in dogs, *Amer. J. Physiol.*, 218:1757 (1970).

Fleisch and Bisaz, Mechanism of calcification: inhibitory role of phyrophosphate, *Nature (Lond.)*, 195:911 (1962).

Fleisch, in Fleisch H, ed., *Bisphosphanates in bone disease: from the laboratory to the patient*, $2^{nd}$ ed. Carnforth, Lancs, England: The Parthenon Publishing Group Ltd., pp. 31–33 (1995).

Ifudo et al., The intensity of hemodialysis and the response to rerythropoietin in patients with end stage renal disease, *N. Engl. J. Med.*, 34:420–425 (1996).

Cheuk et al., Kinetics of pyrophosphate induced iron release from fiferric ovotranferrin, *J. of Inorganic Biochemistry*, 29:301–311 (1987).

Fishbane et al., Reduction in recombinaant human erythropoietin doses by the use of chronic intravenous iron suplementation, *Am . J. Kidney Diseases*, 26:41–46 (1995).

Hurrett et al., Iron fortification of infant cerals: a proposal for the use of ferrous fumarate . . . , *Am. J. Clin. Nutr.*, 49:1274–82 (1989).

Schibler, Inhibition by pyrophosphate and poly–phosphate of aortic calcification induced by vitamin D, in rats, *J. Clin. Sci.*, 35:363–372 (1968).

\* cited by examiner $$\%\text{CHANGE IN TSAT} = \frac{(PostHD) - (PreHD)}{(PreHD)} \times 100$$

METHOD AND PHARMACEUTICAL COMPOSITION FOR IRON DELIVERY IN HEMODIALYSIS AND PERITONEAL DIALYSIS PATIENTS

This is a 371 of PCT/US97/23719, filed Dec. 30, 1997, which is a continuation-in-part of co-pending application Ser. No. 08/775,595 filed Dec. 31, 1996. The benefit of the filing date of provisional application Ser. No. 60/055,315 filed Aug. 7, 1997 is also claimed.

TECHNICAL FIELD

The present invention relates to dialysis and more particularly to methods of supplementing dialysate solutions for the prevention or treatment of iron deficiency in hemodialysis and peritoneal dialysis patients.

BACKGROUND OF THE INVENTION

Patients with chronic renal failure are treated by dialysis. Dialysis is required to maintain homeostasis in patients with end stage kidney failure. Dialysis is defined as the movement of solute and water through a semipermeable membrane which separates the patients blood from the dialysate solution. The semipermeable membrane can either be the peritoneal membrane in peritoneal dialysis patients or an artificial dialyzer membrane in hemodialysis patients.

Patients with chronic renal failure suffer from anemia due to impaired production of erythropoietin [Erslev, 1991]. Clinical manifestations of chronic renal failure improve as uremia and volume overload are corrected by dialysis. However, anemia due to lack of erythropoietin becomes a major limiting factor in the functional well being of end stage renal disease patients.

Molecular cloning of the erythropoietin gene [Jacobs, et al., 1985] led to commercial production of recombinant erythropoietin, which was a major advance in the treatment of renal anemia [Erslev, 1991; Levin, 1992]. Erythropoietin therapy functions by stimulating red cell production and thereby iron utilization. With the use of erythropoietin therapy, transfusions are avoided in most chronic dialysis patients. Blood tests and gastrointestinal bleeding further contribute to loss of iron. Therefore, accelerated iron utilization coupled with small but unavoidable loss of extra corporeal blood with hemodialysis and increased gastrointestinal losses of iron lead to iron deficiency in almost all patients on long term maintenance dialysis.

Other factors that may contribute to an iron deficient state are the restricted renal diet which may be deficient in iron, and iron absorption may be impaired by uremia per se. Co-administration of additional medications, such as phosphate binders with food, may also impair iron absorption. Therefore, iron deficiency has become a major problem in the dialysis patients treated with erythropoietin.

In clinical practice transferrin saturation (ratio of serum iron to total iron binding capacity) and serum ferritin are used to assess the iron status. The majority of maintenance dialysis patients receiving erythropoietin therapy can be arbitrarily classified into six groups depending on their iron status (Table 1).

In states of iron deficiency, iron supply to bone marrow is not maintained and the response to erythropoietin is impaired. Indeed, iron deficiency is the most common cause of erythropoietin resistance [Kleiner et al., 1995]. Uremic patients suffering from absolute or functional iron deficiency require lower doses of erythropoietin if they receive effective iron supplementation. Based on these considerations, Van Wyck et al., [1989] have suggested that all renal patients with low to normal iron stores should prophylactically receive iron. Iron supplementation is accomplished most conveniently by the oral administration of iron one to three times a day.

TABLE 1

Iron Status in End Stage Renal Disease.

| Iron status | Serum Fe/TIBC (TSAT) | Serum Ferritin (μg/L) |
|---|---|---|
| Severe iron deficiency | <15% | <50 |
| Moderate iron deficiency | 15–17% | 50–100 |
| Mild iron deficiency | 18–25% | 100–200 |
| Optimal iron status | 25–50% | 200–800 |
| Iron overload | >50% | >800 |
| Reticuloendothelial block | <20% | >500 |

A problem exists because oral iron is often not tolerated due to gastrointestinal side effects. Practical problems such as noncompliance, impaired absorption when taken with meals, and other factors are further combined with the problem of tolerating oral iron. It is also ineffective due to impaired iron absorption. Macdougall et al.,[1989] also found a retarded response to recombinant human erythropoietin in hemodialysis patients on oral iron, which was corrected once iron was given intravenously. Schaefer and Schaefer [1995], have recently demonstrated that only intravenous but not oral iron, guarantees adequate marrow iron supply during the correction phase of recombinant erythropoietin therapy.

In Europe, iron is available for intravenous administration as iron dextran, iron saccharate and iron gluconate. In the United States, only iron dextran is approved for intravenous use and is widely used for this purpose in dialysis patients. However, there are controversies with regard to the dosage and frequency of injection.

On the one hand, intravenous iron therapy has several advantages over oral administration. Intravenous therapy overcomes both compliance problems and the low gastrointestinal tolerance often observed in patients on oral therapy. Schaefer and Schaefer [1992] reported a 47% reduction in erythropoietin dose when intravenous iron was given to iron deficient hemodialysis patients previously treated with oral iron. On the other hand, intravenous iron therapy does have risks and disadvantages. Anaphylactoid reactions have been reported in patients [Hamstra et al., 1980; Kumpf et al., 1990]. Therefore, a test dose must be administered when parenteral iron therapy is first prescribed. Intravenous iron therapy can also cause hypotension, and loin and epigastric pain during dialysis which may be severe enough to stop the treatment. Further, the intravenous drug is expensive and requires pharmacy and nursing time for administration. With intravenous iron therapy, serum iron, transferrin and ferritin levels have to be regularly monitored to estimate the need for iron and to measure a response to the therapy. Finally, there is also a concern about potential iron overload with intravenous therapy, since the risk of infection and possibly cancer are increased in patients with iron overload [Weinberg, 1984]. Recent evidence further suggests a 35% higher risk for cause-specific infectious deaths in US Medicare ESRD patients given intravenous iron frequently [Collins et al., 1997].

In view of the above, neither the oral nor intravenous iron therapy route is ideal and alternative routes of iron administration are desirable for dialysis patients. The hypotensive effects of intravenous iron dextran are completely abolished, irrespective of the total dose administered, by reducing the rate of infusion or by preliminary dilution of the iron dextran with isotonic saline [Cox et al., 1965]. Addition of an iron compound to the hemodialysis or peritoneal dialysis solutions should lead to a slow transfer of iron into the blood compartment if the dialysis membrane is permeable to the iron salt. Colloidal iron compounds or iron in its mineral form are not soluble in aqueous solutions and therefore not suitable for addition to the dialysate. Furthermore, iron is known to be toxic when administered parenterally in its mineral form. The toxic effects may arise from precipitation of iron in the blood, producing multiple pulmonary and sometimes systemic emboli. Symptoms resembling that of fat embolism occur. Irritation of the gastrointestinal tract gives rise to diarrhea and vomiting. Also, depression of the central nervous system can lead to coma and death [Heath et al., 1982].

Very few noncolloidal iron compounds are suitable for intravenous administration. In the last five years, at least two groups of researchers have administered ferric gluconate sodium intravenously for the treatment of iron deficiency in chronic hemodialysis patients [Pascual et al., 1992; Allegra et al., 1981]. In these and various other studies, solubility, bioavailability and toxicity of various ferric compounds were shown to be different.

Recent studies have shown that polyphosphate compounds are possible candidates for intracellular iron transport [Konopka et al., 1981; Pollack et al., 1985]. Among these polyphosphate compounds, pyrophosphate has been shown to be the most effective agent in triggering iron removal from transferrin [Pollack et al., 1977; Morgan, 1979; Carver et al., 1978]. Pyrophosphate has also been shown to enhance iron transfer from transferrin to ferritin [Konopka et al., 1980]. It also promotes iron exchange between transferrin molecules [Morgan, 1977]. It further facilitates delivery of iron to isolated rat liver mitochondria [Nilson et al., 1984].

Ferric pyrophosphate has been used for iron fortification of food and for oral treatment of iron deficiency anemia [Javaid et al., 1991]. Ferric pyrophosphate has also been used for supplying iron to eukaryotic and bacterial cells, grown in culture [Byrd et al., 1991]. Toxic effects of ferric pyrophosphate have been studied by Maurer and coworkers in an animal model [19901]. This study showed an $LD_{50}$ slightly higher than 325 mg of ferric pyrophosphate per kilogram or approximately 35 milligrams of iron per kilogram body weight. The effective dose for replacing iron losses in hemodialysis patients is estimated to be 0.2 to 0.3 milligrams iron per kilogram per dialysis session. Therefore, the safety factor (ratio of $LD_{50}$ to effective dose) is over 100.

Another metal pyrophosphate complex, stannous pyrophosphate has been reported to cause hypocalcemia and immediate toxic effects. Since ferric ion forms a stronger complex to pyrophosphate than do stannous ion, or calcium ion, [Harken et al., 1981; Sillen et al., 1964], hypocalcemia is not a known side affect of ferric pyrophosphate administration.

The U.S. Pat. No. 4,756,838 to Veltman, issued Jul. 12, 1988, discloses a dry, free flowing, stable readily soluble, noncaking, particulate soluble products which are readily soluble in water and are useful for preparing solutions for use in hemodialysis. The patent discloses the fact that currently used dialysis procedures do not ordinarily take into account those materials in blood that are protein bound. Examples are iron, zinc, copper, and cobalt. The patent states that it is an object of the invention to make such materials as an integral part of dry dialysate products. However, no specific disclosure is made on how to make the iron available through the hemodialysis. No direction is given towards a noncolloidal iron compound as opposed to any other iron compound or mineral iron.

In view of the above, it is desirable to administer iron to a large proportion of dialysis patients by adding a soluble, noncolloidal iron compound to dialysis solutions, in order to replace ongoing losses of iron or to treat iron deficiency. This soluble, noncolloidal iron compound is preferably ferric pyrophosphate.

SUMMARY OF THE INVENTION

In accordance with the present invention, there is provided a method of administering iron in dialysis patients by infusion of a noncolloidal ferric compound, soluble in dialysis solutions, by the process of dialysis. The present invention further provides a pharmaceutical composition consisting essentially of a dialysis solution including a soluble, noncolloidal ferric compound. Preferably, the ferric compound is ferric pyrophosphate.

BRIEF DESCRIPTION OF THE FIGURES

Other advantages of the present invention will be readily appreciated as the same becomes better understood by reference to the following detailed description when considered in connection with the accompanying drawings wherein.

DETAILED DESCRIPTION OF THE INVENTION

In accordance with the present invention, a method is provided for the administration of a soluble, noncolloidal ferric compound to dialysis patients during the dialysis treatment. This administration can be utilized for patients on hemodialysis (acute or maintenance) or peritoneal dialysis (acute or maintenance).

More specifically, as discussed above, dialysis patients are those patients undergoing hemodialysis or peritoneal dialysis for renal failure. Long-term dialysis therapy for treatment of end stage renal failure is referred to as maintenance dialysis. Patients on maintenance hemodialysis have been estimated to lose about 2 to 3 grams of iron per year, corresponding to approximately 6 ml per day (2 liters per year) blood loss from all sources [Eschbach et al., 1977]. These patients generally receive hemodialysis three times per week.

A specific example of a hemodialysis system is the Fresenius system. In the Fresenius system, the ratio of acid:bicarbonate:water:total is 1:1.23:32.77:35. Therefore, one part of the concentrated bicarbonate solution is mixed with 27.5 parts of the other (acid+water), to make the final dialysate. In order to make the bicarbonate concentrate, purified water is pumped from the purified water source into a large tank. Fresenius supplies sodium bicarbonate powder packaged in plastic bags and the contents of each bag are mixed with purified water in the tank, to make 25 gallons (94.6 liters) of bicarbonate solution. After thoroughly mixing with a stirrer, the concentrated solution is run into plastic receptacles. The concentrate is prepared within 24 hours of its use. Ferric pyrophosphate is freely soluble in the bicarbonate concentrate. Ferric pyrophosphate may be added in a dry or solution form to the dialysis concentrate. For a dialysate iron concentration of 4 $\mu$g/dl or FePyP concentration of 40 $\mu$g/dl, it can be calculated that bicarbonate concentrate should have a ferric pyrophosphate concentration of 40×27.5=1100 $\mu$g/dl, or 11 mg/liter. Therefore, 1040 mg of ferric pyrophosphate added to 94.6 liter (25 gallons) of bicarbonate concentrate will generate a dialysate with an iron concentration of 4 $\mu$g/dl.

TABLE 2

Bicarbonate concentrates with a defined iron concentration achieved by addition of FePyP.

| Required Conc. of Fe in dialysate | Estimated Conc. of FePyP in dialysate | Estimated Amount of FePyP in concentrate |
|---|---|---|
| 2 $\mu$g/dl | 20 $\mu$g/dl | 5.5 mg/L |
| 4 $\mu$g/dl | 40 $\mu$g/dl | 11 mg/L |
| 8 $\mu$g/dl | 80 $\mu$g/dl | 22 mg/L |
| 12 $\mu$g/dl | 120 $\mu$g/dl | 33 mg/L |

Dialysate Fe concentration can be increased by adding different amounts of FePyP to the bicarbonate concentrate (Table 2). Ferric pyrophosphate may be added to the dialysate concentrate either in its crystalline form or as an aqueous solution.

Figure 1A:
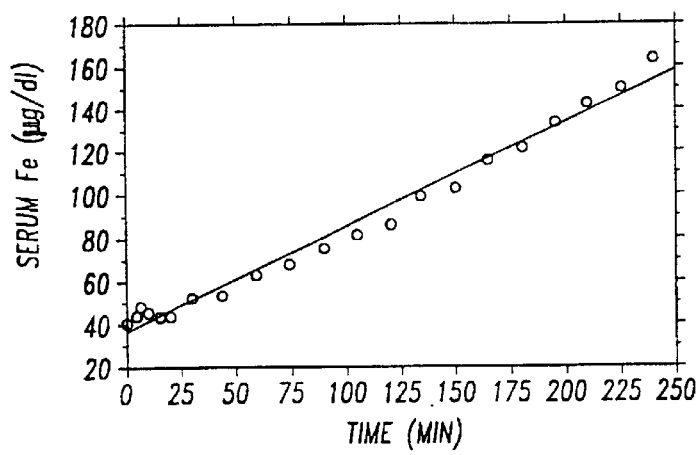
FIG. 1 is a pair of graphs showing serum iron versus time and iron per TIBC (percent) versus time.
Figure 1B:
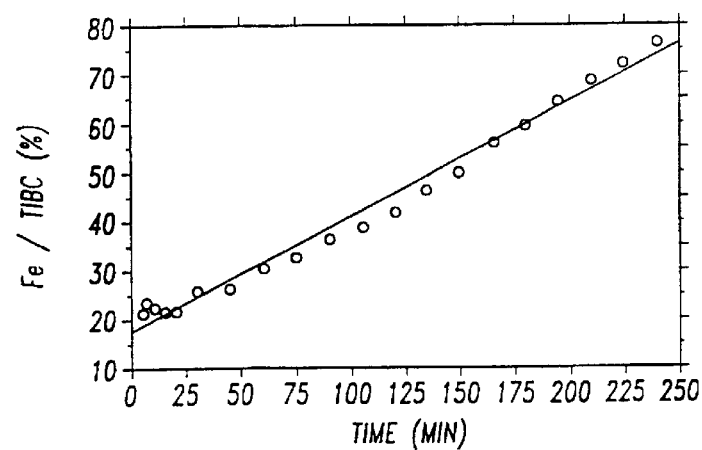

As shown in Example 1 herein below, plasma (3.5 liters) was dialyzed in vitro using an F-80 dialyzer with the plasma flow rate set at 300 ml/min. and the dialysate flow rate 800 ml/min. Ferric pyrophosphate (420 mg) was added to 20 liters of bicarbonate concentrate and intermittently stirred for one hour prior to the dialysis. This was a clear solution with a light greenish yellow tinge. The final dialysate was a clear, colorless solution, with 5 $\mu$g/dl iron content, as measured by a calorimetric assay. Physiological saline solution was added to the plasma every 15 minutes to compensate for obligate ultrafiltration, and to keep the plasma volume constant. Serum Fe and TIBC were measured at frequent intervals. There was a progressive increase in serum iron concentration (A), and transferrin saturation (B), as shown in FIG. 1.

Figure 2:
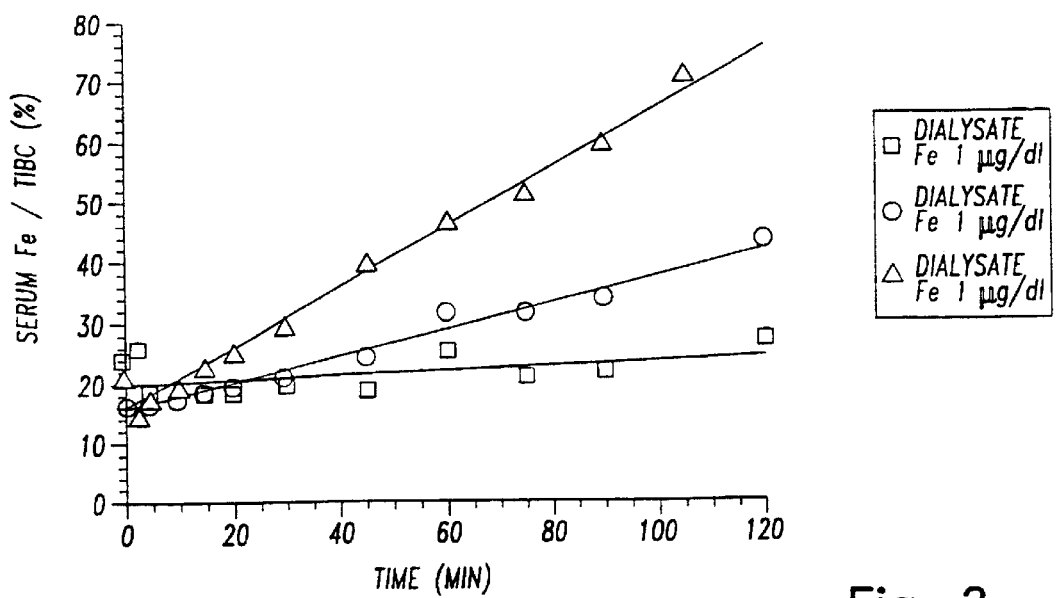
FIG. 2 is a graph showing serum iron per total iron binding capacity (TIBC) (percent)
Figure 3:
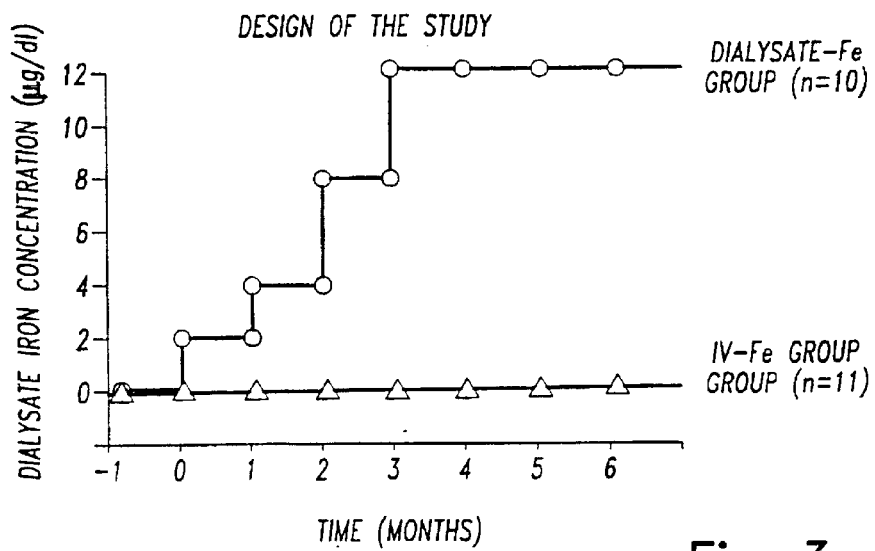
FIG. 3 is a graph showing the study design and concentration of iron in the dialysate over the study period.

In a separate experiment, in vitro dialysis was performed using three different concentrations of ferric pyrophosphate in the dialysate. Under otherwise identical experimental conditions, the increment in transferrin saturation was dependent on the dialysate iron concentration (FIG. 2).

Dialysis is defined as the movement of solute and water through a semipermeable membrane (the dialyzer) which separates the patient's blood from a cleansing solution (the dialysate). Four transport processes may occur simultaneously during dialysis.

1. Diffusive transport is the movement of solutes across the membrane, and is dependent on the concentration gradient between plasma water and dialysate;
2. Convective transport is the bulk flow of solute through the dialyzer in the direction of hydrostatic pressure difference;
3. Osmosis is the passage of solvent (water) across the membrane in the direction of the osmotic concentration gradient; and
4. Ultrafiltration is the movement of solute free water along the hydrostatic pressure gradient across the membrane.

The patient's plasma tends to equilibrate with the dialysate solution over time. The composition of the dialysate permits one to remove, balance or even infuse solutes from and into the patient. The electrochemical concentration gradient is the driving force that allows the passive diffusion and equilibration between the dialysate and the patient's blood compartment. The process of dialysis can be accomplished by using an artificial kidney (hemodialysis and hemofiltration) or patient's abdomen (peritoneal dialysis).

In an artificial kidney, a synthetic or semi-synthetic semipermeable membrane made of either cellulose acetate, cuprophane, polyacrilonitrile, polymethyl methacrylate, or polysulfone is used. A constant flow of blood on one side of the membrane and dialysate on the other allows removal of waste products. An artificial kidney can be used to perform hemodialysis, during which diffusion is the major mechanism for solute removal. On the other hand hemofiltration (also called hemodiafiltration and diafiltration) relies on ultrafiltration and convective transport rather than diffusion to move solutes across a high porosity semipermeable membrane. For the purposes of this application, the term hemodialysis is used to include all dialysis techniques (e.g. hemofiltration) that require an extracorporeal blood circuit and an artificial membrane.

On the other hand, peritoneal dialysis uses patient's peritoneal membrane to exchange solutes and fluid with the blood compartment. Therefore, peritoneal dialysis is the treatment of uremia by the application of kinetic transport of water-soluble metabolites by the force of diffusion and the transport of water by the force of osmosis across the peritoneum. The peritoneum is the largest serous membrane of the body (approximately 2 m² in an adult). It lines the inside of the abdominal wall (parietal peritoneum) and the viscera (visceral peritoneum). The space between the parietal and visceral portions of the membrane is called the "peritoneal cavity". Aqueous solutions infused into the cavity (dialysate) contact the blood vascular space through the capillary network in the peritoneal membrane. The solution infused into the peritoneal cavity tends to equilibrate with plasma water over time and it is removed at the end of one exchange after partial or complete equilibration. The composition of the dialysate permits to remove, balance or even infuse solutes from and into the patient. The electrochemical concentration gradient is the driving force that allows the passive diffusion and equilibration between the dialysate and blood compartment.

The dialysis solutions (hemodialysis or peritoneal dialysis) of the present invention are characterized by an added noncolloidal ferric compound, preferably having a molecular weight of less than 5000 daltons. Optimally, the ferric compound should be 1) soluble in dialysis solutions in adequate concentrations; 2) efficiently transfer from the dialysate to the blood compartment; 3) bind to transferrin in the plasma and be available for use by tissue; 4) be well tolerated without any short or long term side effects; and 5) be economical. Ferric pyrophosphate seems to possess all the above characteristics and therefore is the preferred iron compound for use with the present invention, though other soluble ferric compounds may also be used.

Ferric pyrophosphate ($Fe_4O_{21}P_6$) has a molecular weight of 745.25. It is a nonahydrate with yellowish-green crystals. It has been used as a catalyst, in fireproofing synthetic fibers and in corrosion preventing pigments.

Presently, hemodialysis machines utilize an automated proportioning system to mix salts in deionized water in specific proportions to generate the final dialysate solution. The dialysate concentrates are usually supplied by the manufacturer either as a solution ready to use or as a premixed powder that is added to purified water in large reservoirs. The concentrates are pumped into a chamber in the dialysis machine where they are mixed with purified water to make the final dialysate solution.

Generally, the ionic composition of the final dialysate solution for hemodialysis is as follows: $Na^+$ 132–145 mmol/L, $K^+$ 0–4.0 mmol/L, $Cl^-$ 99–112 mmol/L, $Ca^{++}$ 1.0–2.0 mmol/L, $Mg^{+2}$ 0.25–0.75 mmol/L, Glucose 0–5.5 mmol/L. The correction of metabolic acidosis is one of the fundamental goals of dialysis. In dialysis, the process of H+ removal from the blood is mainly achieved by the flux of alkaline equivalents from the dialysate into the blood, thereby replacing physiological buffers normally utilized in the chemical process of buffering. In dialysis practice, base transfer across the dialysis membrane is achieved by using acetate or bicarbonate containing dialysate. In "Bicarbonate dialysis" the dialysate contains 27–35 mmol/L of bicarbonate and 2.5–10 mmol/L of acetate. On the other hand, in "Acetate dialysis" the dialysate is devoid of bicarbonate and contains 31–45 mmol/L of acetate. Ferric pyrophosphate is compatible with both acetate and bicarbonate based hemodialysis solutions.

The peritoneal dialysis fluid usually contains $Na^+$ 132–135 mmol/L, $K^+$ 0–3 mmol/L, $Ca^{++}$ 1.25–1.75 mmol/L, $Mg^{++}$ 0.25–0.75 mmol/L, $Cl^-$ 95–107.5 mmol/L, acetate 35 mmol/L or lactate 35–40 mmol/L and glucose 1.5–4.25 gm/dL. Ferric pyrophosphate is soluble and compatible with peritoneal dialysis solutions.

In accordance with the present invention, ferric pyrophosphate is either added directly to peritoneal dialysis solutions, or to the concentrate for hemodialysis. In case of hemodialysis, since the concentrates are diluted several fold in the machine by admixture with water, the compound has to be added at a proportionally higher concentration in the concentrate.

Preferably, 2 to 25 $\mu$g of the ferric iron (as ferric pyrophosphate) per deciliters of the hemodialysis solution is used for hemodialysis. Accordingly, 4 to 50 milligrams of iron are infused into the patient during a two to five hour hemodialysis session. Currently, hemodialysis patients number 230–250,000 in the United States and about one million worldwide. The majority of these patients are require erythropoietin therapy to maintain hemoglobin in the target range of 10–12 gm/dL. Although, all patients on dialysis treated with erythropoietin are prescribed oral iron therapy, only 45% maintain transferrin saturation levels above 20 percent with oral iron therapy [Ifudu et al., 1996]. It has been documented that at least one-half of the hemodialysis population requires intravenous iron to maintain iron balance [Sepandj et al., 1996]. Even though dialysate iron therapy is potentially useful for all hemodialysis patients, those requiring intravenous iron are more likely to benefit. To evaluate whether dialysate iron therapy is more economical than the conventional therapies, a comparative cost analysis for one patient year of hemodialysis was performed. It is estimated that a maximum of 1 gram of ferric pyrophosphate may need to be added to 20 liters of bicarbonate concentrate which is utilized during a single dialysis procedure. A total of 156 grams of ferric pyrophosphate will be added to the dialysate per patient year. The cost of FePyP is $25.00 per kg (Mallinckrodt Baker, Inc., Chesterfield, Mo.), and therefore, the annual cost of FePyP is estimated to be approximately $5.00 per patient year. It is evident that dialysate iron therapy is more economical than intravenous iron.

As shown in Example 2 herein below, the efficacy and safety of ferric pyrophosphate added to the dialysate is shown. Uremic patients on chronic hemodialysis, receiving regular maintenance intravenous iron were randomized into two groups. One cohort was selected to receive dialysate iron therapy, accomplished by adding soluble ferric pyrophosphate to the dialysate. The other cohort was continued on regular maintenance intravenous iron dextran. At baseline, there were no significant differences in the two groups as regards demographics, comorbid conditions (hypertension/diabetes), nutritional parameters (body weight, albumin, lipids), iron parameters, and requirements for erythropoietin or intravenous iron dextran. In this dose finding study, after six months of observation, the only significant difference between the two groups was a decline in intravenous iron requirement in the dialysate iron group (P=0.002). No adverse effects related to dialysate iron were identified. In conclusion, addition of iron to the dialysate as ferric pyrophosphate, is a safe and effective method of iron administration to hemodialysis patients. Dialysate iron therapy is able to maintain iron balance in the majority of hemodialysis patients without a need for oral or intravenous iron supplementation. In a minority of patients receiving dialysate iron therapy, the requirement for intravenous iron is significantly reduced but not completely eliminated.

In view of the above, the present invention provides pharmaceutical composition of a soluble, noncolloidal ferric compound that can be added to dialysis solutions to meet the iron supplementation or therapeutic needs of dialysis patients. However, some dialysis patients may still need oral or intravenous iron supplements.

The following Examples demonstrate the preparation and utility of the present invention.

EXAMPLE 1

In Vitro Studies on the Solubility of Ferric Pyrophosphate in Dialysis Solutions Ferric pyrophosphate ($Fe_4(P_2O_7)_3$, M.W. 745.2, CAS 10058-44-3) (hereinafter FePyP) is a greenish yellow, crystalline compound that is known to have a solubility of 50 mg per ml. in warm water (Catalog no. P 6526; Sigma Chemical Co., St. Louis, Mo.). Initially, a small amount of FePyP crystals were added to the acid (pH, 2.49) and basic (pH, 7.81) concentrates and a bicarbonate dialysate (pH, 7.15). FePyP dissolved readily in the bicarbonate dialysate and the bicarbonate concentrate, forming a yellow-orange solution. However, there was incomplete dissolution in the acid concentrate, where a precipitate was clearly visible. Since the concentrated bicarbonate

TABLE 3

Concentration of iron in bicarbonate concentrate after the addition of ferric pyrophosphate

| Amount of FePyP added | Expected iron conc. | Measured conc. of Fe |
|---|---|---|
| 2 mg/ml | 0.2 mg/ml or 20 mg/dl | 20.250 mg/dl |
| 5 mg/ml | 0.5 mg/ml or 50 mg/dl | 40.660 mg/dl |
| 10 mg/ml | 1.0 mg/ml or 100 mg/dl | 94.500 mg/dl |
| 20 mg/ml | 2.0 mg/ml or 200 mg/dl | 206.500 mg/dl |

*note ~10% of FePyP is Fe solution is diluted several fold in the formation of the final dialysate, the concentration of FePyP in the bicarbonate concentrate should be appropriately higher than the desired dialysate concentration. Therefore, solubility of FePyP in the bicarbonate concentrate was tested by adding variable amounts of FePyP and measuring the iron content of the mixture by a standard calorimetric method. The results are shown in Table 3. The measured and expected concentrations of iron were similar, showing that FePyP is highly soluble at the concentrations tested. In dialysis practice, dialysate with a specific concentration of FePyP can be generated using a bicarbonate concentrate containing a proportionately higher concentration of FePyP. Similar experiments were performed using the acetate concentrate for hemodialysis and ferric pyrophosphate was found to be soluble and compatible with acetate based dialysis solutions.

In Vitro Hemodialysis with Dialysis Solutions Containing Ferric Pyrophosphate In a second set of experiments, an in vitro dialysis of plasma, utilizing a conventional hemodialysis set up was used to show that the addition of even small amounts of ferric pyrophosphate to a dialysate solution, results in significant transport of iron into the blood compartment during dialysis. This occurs because the transferred iron avidly binds to transferrin in the plasma.

A. Methods

Plasma was obtained from a uremic patient undergoing plasma exchange therapy for Goodpastures syndrome. Citrated plasma was stored at −20° C. in plastic bags. In three separate experiments, plasma was dialyzed against dialysates with different concentration of Fe, prepared by adding variable amounts of FePyP to the bicarbonate concentrate. Dialyzers with a polysulfone membrane (Fresenius, USA) were used. When the volume of plasma being dialyzed was less than 1000 ml, a small dialyzer (F-4, Fresenius) with small blood volume (65 ml) and surface area (0.8 sq. meter) was used at a plasma flow rate of 100 ml/min. With a larger volume of plasma, a F-80 dialyzer with a priming volume of 120 ml and a surface area of 1.8 sq. meter was used at a plasma flow rate of 300 ml/min. Heparin (500 units per hour) was infused to prevent clotting in the circuit. Serum was drawn at regular intervals during the experiment and serum iron (Fe), total iron binding capacity (TIBC) and transferrin saturation (Fe/TIBC×100) were measured by a calorimetric assay. The obligate ultrafiltration of fluid during hemodialysis was compensated by a continuous infusion of 0.9% saline. The iron parameters were corrected for net ultrafiltration by expressing the results as transferrin saturation.

B. Results

There was an increase in serum iron and transferrin saturation with time when iron was added to the dialysate (FIGS. 1 and 2). The increment in serum Fe and transferrin saturation was more as the concentration of iron in the dialysate was increased (FIG. 2). There was a near doubling of transferrin saturation after two hours of dialysis with a dialysate iron concentration of 8 µg/dl (FIG. 2).

Experimental parameters were chosen to mimic conditions that prevail in actual dialysis practice. Therefore, 3.5 liters of plasma (approximating the plasma volume in a 70 kg. patient) was dialyzed against a dialysate with 5 µg/dl Fe concentration. The results are shown in FIG. 1.

The hourly increase in plasma iron concentration was 23, 23, 35 and 45 µg/dl, and the net increase in iron concentration was 140 µg/dl over the course of the experiment. Therefore, 5 mg iron (or ~50 mg FePyP) was infused into 3.5 liters of plasma, using a dialysate with 5 µg iron per dl.

In conclusion, ferric pyrophosphate can be added to the bicarbonate concentrate, to attain iron concentrations of 2–50 µg/dl in the final dialysate to meet various levels of Fe deficiency in patients. Hemodialysis with iron containing dialysate does result in transfer of iron to the blood compartment. In these in vitro experiments, maximum iron transfer cannot be obtained since transferrin is confined to a closed system. In vivo, the release of iron to the erythron in the bone marrow and to the tissues by transferrin, increases the total amount of iron that can enter the blood compartment. Thus, dialysate iron therapy is a safe and effective route of iron delivery to hemodialysis patients. In view of the above experiments, it is clear that hemodialysis utilizing a hemodialysis solution containing iron compounds such as ferric pyrophosphate, can be used to increase the amount of bioavailable iron in a mammal. The data demonstrates that the ferric pyrophosphate is soluble in hemodialysis solutions in adequate concentrations, efficiently transfers from the dialysate to the blood compartment, and binds to the transferrin in the plasma. This data combined with previous studies showing the safety of ferric pyrophosphate, demonstrates the utility of the present invention as a means for providing bioavailable iron in a mammal, but more specifically in dialysis patients requiring oral or parenteral iron supplementation.

EXAMPLE 2

Administration of Iron to Hemodialysis Patient by Dialysis, using Dialysis Solutions Containing Soluble Iron: a Phase I/II Clinical Study A. Design of the Study To determine a safe and effective dose of dialysate iron, a cohort of chronic hemodialysis patients were dialyzed with ferric pyrophosphate containing dialysate, while contemporaneous controls received regular doses of intravenous iron, in an open label, phase I/II clinical trial. All subjects in the study were receiving maintenance hemodialysis for end stage kidney failure, and requiring erythropoietin and intravenous iron to maintain hemoglobin in the 10–12 gm/dl range. After obtaining an informed consent, patients were enrolled and oral iron was discontinued. All patients received maintenance intravenous iron (50–100 mg every 1–2 weeks) during a 4 week long pre-treatment phase. The last two weeks of this pre-treatment period were used to establish the "Baseline" serum iron and hematological parameters. In the Treatment Phase, ten patients were dialyzed with iron containing dialysate (Dialysate-Fe group) for a period of 4 months. The concentration of iron in the dialysate was 2 $\mu$g/dl during the first 4 weeks, and was progressively increased every 4 weeks to 4, 8, and 12 $\mu$g/dl. Since adverse reactions were not experienced even with the maximum concentration, the trial utilizing 12 $\mu$g/dl dialysate iron was extended by an additional 2.5 months. Eleven control patients (IV-Fe Group) continued to receive 50–200 mg iron intravenously every 1–2 weeks, for the entire study period of 6.5 months.

The doses of intravenous iron dextran were adjusted based on the serum ferritin and transferrin saturation. The initial doses were 50 mg elemental iron weekly. The doses were increased to 100 mg if transferrin saturation was less than 25% or serum ferritin was less than 200 $\mu$g/L. The dose was reduced to 50 mg weekly when these parameters were exceeded.

If serum transferrin saturation were to exceed 60% or serum ferritin were to exceed 1500 $\mu$g/dl, the administration of intravenous or dialysate iron was discontinued. On the other hand, if any patient demonstrated evidence of a severe iron deficiency (i.e. transferrin saturation <15% or serum ferritin <50 $\mu$g/L), the subject was treated for iron deficiency by intravenous administration of 100–200 mg iron with each dialysis session up to a total dose of 500–1000 mg at the discretion of the Inventor. Increased availability of iron to marrow cells may improve responsiveness to erythropoietin, thereby raising the hemoglobin and hematocrit. Hemoglobin and hematocrit were monitored every week, and in the event of improved erythropoiesis, the doses of erythropoietin were reduced by 10% every two weeks or as needed, to maintain a stable hemoglobin.

B. Choice of the Control Group

According to the National Kidney Foundation-Dialysis Outcomes Quality Initiative (NKF-DOQI) recommendations, most hemodialysis patients should be administered intravenous iron with every dialysis session or every 1–2 weeks (maintenance therapy). NKF-DOQI guidelines do not recommend continuation of oral iron supplements in chronic hemodialysis patients on maintenance intravenous iron. This was the basis why the control group was maintained on regular doses of intravenous iron, while oral iron was discontinued. This being the standard of care, the subjects on maintenance intravenous iron (IV-Fe Group) served as the control against the experimental group receiving dialysate iron therapy (Dialysate-Fe Group).

C. Study Population

The study population was randomly selected from all patients undergoing maintenance hemodialysis at Clara Ford Dialysis unit. Patients who met the inclusion and exclusion criteria, as described below, were eligible for entry into the pre-treatment phase of the study only after the nature and purpose of the protocol had been explained to them and after they had voluntarily granted written informed consent to participate.

1. Inclusion Criteria: Only patients meeting all of the following criteria were eligible for entry into the pre-treatment phase of the study:

Patients who have voluntarily signed an informed consent;

Patients aged 18 years or older;

Patients with end stage renal disease undergoing maintenance hemodialysis, who are expected to remain on hemodialysis and be able to complete the study. Because of the relatively brief study period patients on cadaveric transplant list are not excluded.

Patients, if female, must be either ammenorrheic for a minimum of one year, or using an effective birth control method;

Patients with a mild iron deficiency (transferrin saturation between 18 to 25% and serum ferritin 100–200 $\mu$g/L), and therefore eligible for maintenance intravenous iron therapy in normal clinical practice.

2. Exclusion Criteria Patients exhibiting any of the following characteristics were excluded from entry into the study:

Patients with severe iron deficiency defined as a transferrin saturation <15% and/or serum ferritin <50 $\mu$g/L;

Patients who are able to maintain adequate iron stores (transferrin saturation >25% and serum ferritin >200 $\mu$g/L) without parenteral iron therapy;

Patients with a history of clinically significant allergic reaction to iron;

Patients with malignancy or overt liver disease;

Patients with a history of drug or alcohol abuse within the last 6 months;

Patients considered to be incompetent to give an informed consent;

Patients who are anticipated to be unable to complete the entire study (e.g. concurrent disease);

Patients with hepatitis B, or HIV infection;

Patients who are pregnant or breast feeding;

Female patients who menstruate and are unwilling/unable to use a safe and effective birth control method to prevent pregnancy during the study period.

A random number generator was used to generate a list of 24 numbers. Odd and even numbers were assigned A or B designation respectively. A list of 23 patients was created based on the order in which consent was obtained for participation in the study. Patients were assigned to groups A or B based on their order in the list. Twenty-two patients entered the Treatment Phase. One patient in the dialysate iron group elected to withdraw from the study due to lack of interest on the first day of the treatment phase. The remaining twenty-one patients completed the study.

D. Dose Selection

1. Dose Selection for Dialysate-Fe Group

The preliminary data obtained from in vitro testing of iron transfer across the membrane when FePyP is added to the dialysate was used to select doses in this trial (see Example 1). When a relative iron deficiency was suspected bolus doses of 100–200 mg iron were administered intravenously with each dialysis, over 1–5 consecutive dialysis sessions.

2. Dose Selection for IV-Fe Group

Based on the NKF-DOQI guidelines, patients in IV-Fe group were prescribed maintenance amount of intravenous iron from 25 to 100 mg/week. When a relative iron deficiency was suspected, bolus doses of 100–200 mg iron were administered intravenously with each dialysis, over 5–10 consecutive dialysis sessions.

E. Effectiveness and Safety Variables Recorded

1. Effectiveness This variable was measured by

Monitoring the hemoglobin/hematocrit and iron parameters.

Monitoring the dose of intravenous iron and erythropoietin in the two groups.

2. Safety Variables The following safety variables were measured and/or monitored frequently.

Frequent monitoring of vital signs to detect any cardiovascular toxicity, respiratory toxicity or hypersensitivity reactions.

Directed history and physical examination prior to any increment in the dialysate iron dose.

Hemoglobin (for diagnosis of anemia)

Iron parameters (for detection of iron deficiency or toxicity)

Liver function tests (to detect hepatotoxicity)

Nutritional parameters such as weight, albumin, cholesterol and triglycerides were measured to detect malnutrition.

Serum electrolytes.

Serum calcium and inorganic phosphorus: to detect any potential hypocalcemia or hyperphosphaemia secondary to ferric pyrophosphate administration.

F. Criteria for Effectiveness of Dialysate Iron Therapy

Experimental therapy will be considered effective, if the patients receiving iron in the dialysate, when compared with patients receiving maintenance intravenous iron;

maintain hemoglobin level, without an increase in erythropoietin dose; and maintain adequate iron stores and did not develop iron deficiency despite a reduced need for intravenous iron. The three important tests of iron deficiency that were monitored in the study were TSAT (transferrin saturation), reticulocyte hemoglobin (Retic Hgb, a measure of the prevailing iron availability to the bone marrow) and serum ferritin (a measure of the tissue stores).

G. Concomitant therapy

Oral iron was discontinued in both groups.

Patients in the dialysate-Fe group received supplemental doses of intravenous iron when clinically indicated.

Patients in both groups received blood transfusions when clinically indicated.

H. Statistical Methods and Analysis

Except for plotting of individual patient variables over time, the iron study data has been summarized prior to analysis. Descriptive analysis was performed. Most of the analysis presented here, uses the data averaged over four or six/seven week intervals. A four week interval corresponds to the length of time each dose level was used during the dose escalation phase of the study. However, the final study interval used was six or seven weeks long, since the final data collection did not take place until twenty-six or twenty-seven weeks after the start of the intervention. (See Figures 4–21)

The baseline period, labeled month 0, included data for the four weeks immediately prior to the start of the intervention. (There was some data available for some or all the fifth week prior to the intervention, but data from this week is omitted from the formal data analysis.)

Weeks 1 to 4, when the dialysate dose of 2 $\mu$g/dl was employed, are labeled month 1, weeks 5 to 8 labeled month 2, weeks 9 to 12 labeled 'month 3', weeks 13 to 16 labeled month 4, weeks 17 to 20 labeled month 5, and weeks 21 to 26 (or 27) are labeled month 6.

Treatment doses, serum ferritin and transferrin saturation were plotted over time for each patient in each group. The proportion of patients who achieved optimal iron status in each group were computed as well as the average time required for this. Average serum ferritin and transferrin saturation levels were computed for each group at each time point.

The differences in mean serum ferritin and transferrin saturation levels were computed along with their 95% confidence intervals at each time point. The proportions of patients showing side effects, either serious or minor were noted for each group at each time point.

Baseline demographic and nutritional status variables were analyzed from separate data sets. The nutritional parameters: weight, albumin, cholesterol and triglycerides were entered only once for each study month.

Data on instances of complications, medications and procedures was extracted from the Greenfield Health System database which contains routinely collected clinical information. For each variable the data was summarized as the count of days for a 4-week month, for which a complication, medication administration or procedure was performed. If multiple instances occurred on a single day, this was counted as only one occurrence. Due to the infrequency of many of these variables, this data was summarized for the baseline month(0), for all 6 study months(1–6), and for the final observation month(6).

Data on pre- and post-hemodialysis weights and blood pressures, along with blood pressures recorded at times of complications during hemodialysis was extracted from the Greenfield Health System database which contains routinely collected clinical information. The blood pressures were summarized by extracting the minimum and maximum for a session, since instances of hypotension and/or hypertension would be of interest.

I. Results of the Study

1. Demographics and Baseline of Individual Patients and Comparability of Treatment Groups Baseline characteristics of the 2 groups are shown in Table 4. None of the baseline differences were statistically significant.

TABLE 4

Characteristics of 21 patients included in the final analysis

| Variable | Dialysate-Fe (Group A) | IV-Fe (Group B) | p value |
| --- | --- | --- | --- |
| Demographics | | | |
| Age (years) | 53.5 ± 14.3 | 58.1 ± 15.5 | 0.489 |
| Gender (Male) | 6 (60%) | 7 (64%) | 0.788 |
| Race (Black) | 9 (90%) | 11 (100%) | 0.283 |
| Co-morbid disease | | | |
| Hypertension | 10 (100%) | 11 (100%) | 1.000 |
| Diabetes Mellitus | 6 (60%) | 7 (64%) | 0.864 |
| Nutritional Status | | | |
| Albumin | 3.8 ± 0.45 | 3.8 ± 0.38 | 0.870 |
| Cholesterol | 161.4 ± 19.8 | 153.2 ± 32.9 | 0.502 |
| Triglycerides | 156.8 ± 75.5 | 143.7 ± 73.8 | 0.693 |
| Dry Weight | 84.3 ± 17.7 | 81.0 ± 35.3 | 0.788 |

2. Hematological and Iron Parameters

Figure 4:
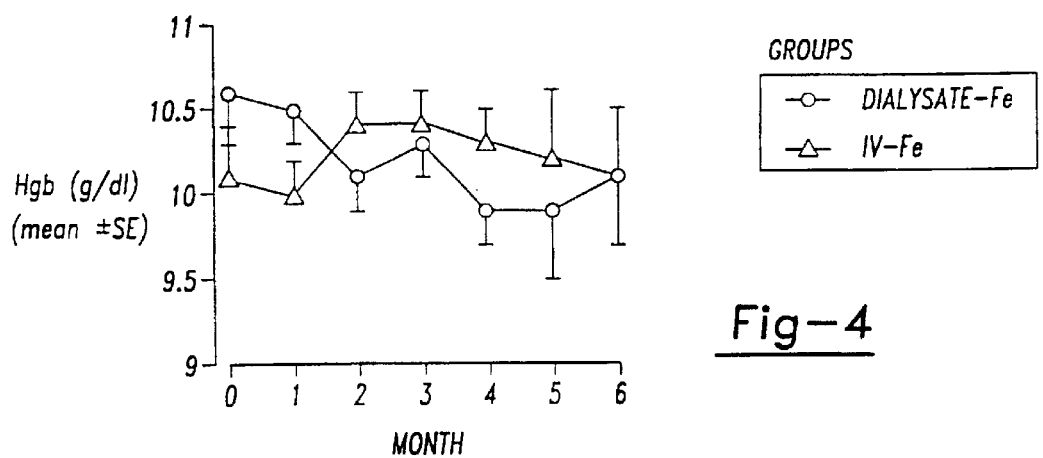
FIG. 4 is a graph of group whole blood hemoglobin average over the study period.
Figure 9:
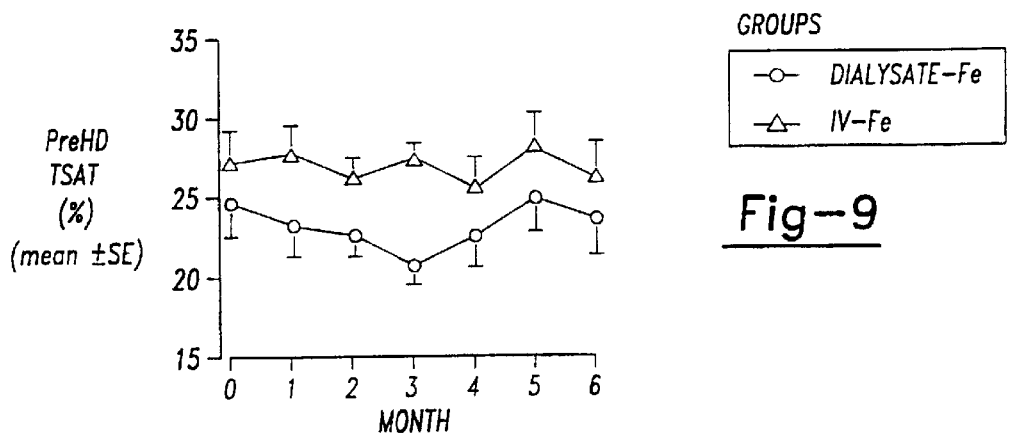
FIG. 9 is a graph of the group predialysis transferrin saturation (TSAT) average over the study period.
Figure 13:
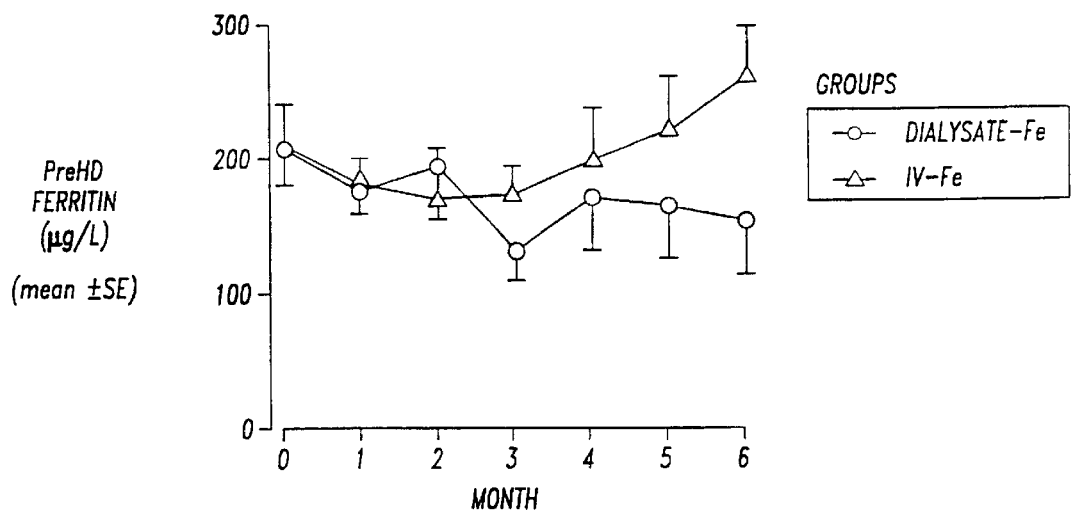
FIG. 13 is a graph of the group predialysis ferritin average over the study period.

During the study, the dose of erythropoietin and intravenous iron were adjusted and prescribed by the investigators so that hemoglobin/hematocrit and iron parameters (transferrin saturation and ferritin) would stay in the target range. In either group, there was no significant change in hemoglobin or TSAT/ferritin when parameters at the month '6' were compared with the baseline (FIGS. 4, 9 and 13). Furthermore, when the 2 groups were compared there was no significant differences in hemoglobin (FIG. 4), pre-dialysis serum iron, (FIG. 6), TSAT (FIG. 9), or ferritin (FIG. 13) at months 0–6.

Figure 5:
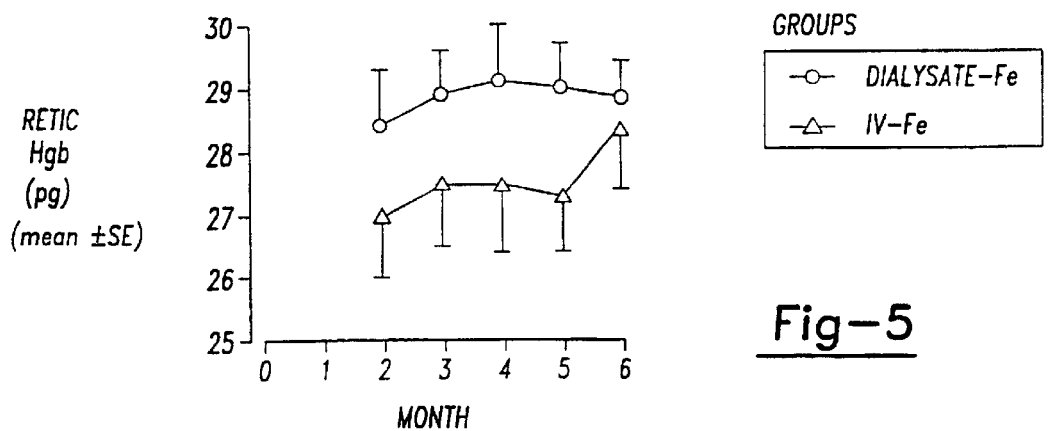
FIG. 5 is a graph of the group reticulocyte hemoglobin average amount over the study period.
Figure 6:
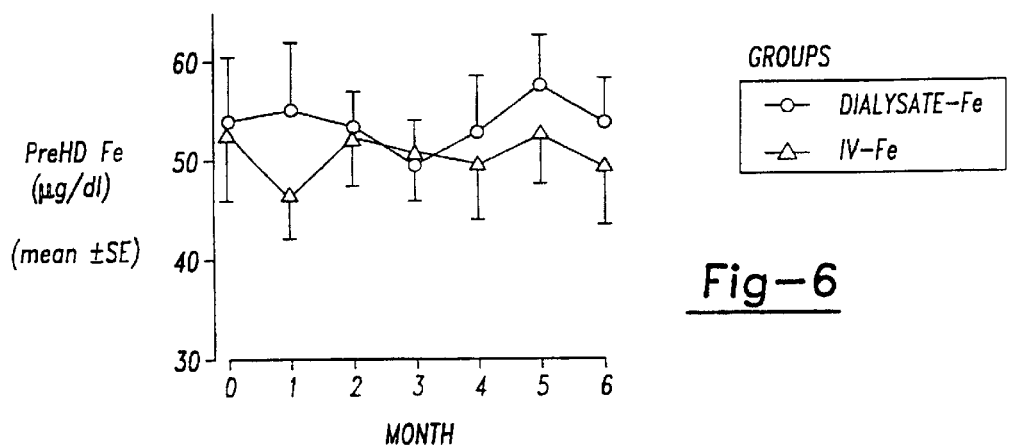
FIG. 6 is a graph of the group predialysis serum iron level average over the study period.

Testing for 'reticulocyte hemoglobin' (Retic-Hgb) was not available during months '0–1', and consequently Retic-Hgb was measured only in months '2–6'. At month '2', Retic-Hgb was 28.4±0.9 pg in Dialysate-Fe groups vs. 27.0±1.0 pg in IV-Fe group (p<0.1). In both groups, Retic-Hgb did not change significantly during the course of the study (FIG. 5).

b. Erythropoietin Dose

Figure 14:
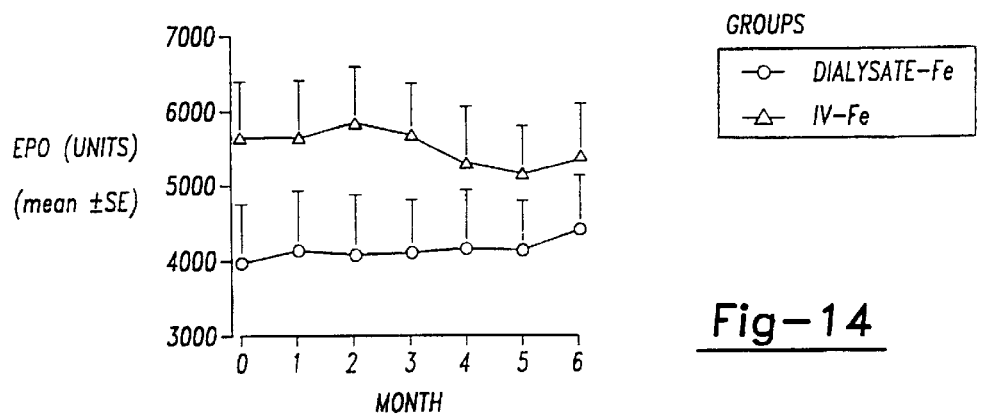
FIG. 14 is a graph of the group erythropoietin dose per treatment average over the study period.

The dose of erythropoietin did not change significantly during the study, in the 2 groups (FIG. 14). Furthermore, there was no significant difference in the erythropoietin requirement between the two groups either at baseline or at any time during the study.

c. Dose of IV Iron (Infed®)

Figure 15:
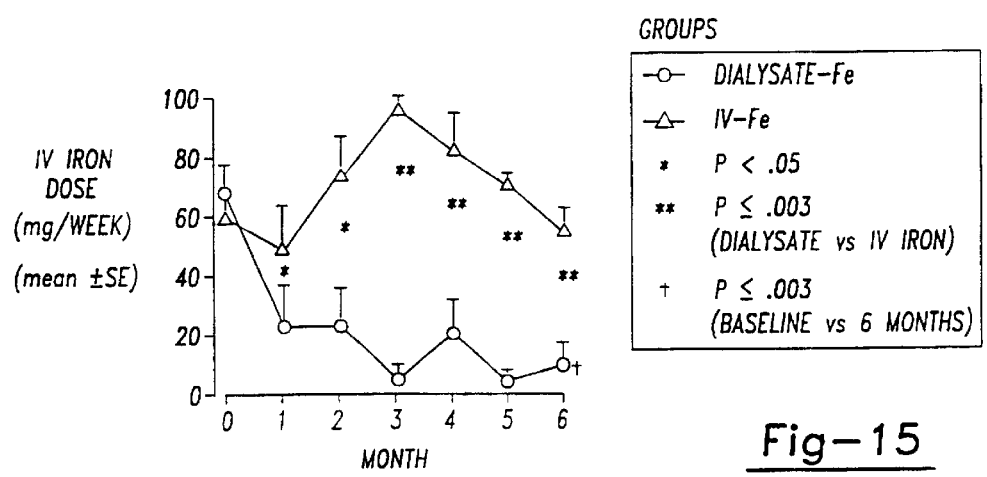
FIG. 15 is a graph of the group weekly dose of intravenous iron (Infed®) average over the study period.

During the pretreatment period (month '0'), the average weekly dose of intravenous iron was 59.6 mg in the IV-Fe group and 68.7 mg in the Dialysate-Fe group (FIG. 15). Despite no significant difference in hemoglobin, transferrin saturation, ferritin or erythropoietin dose between the 2 groups, the requirement for intravenous iron was significantly reduced with dialysate iron (p≦0.002 with 8–12 µg/dl dialysate iron).

The average weekly doses of intravenous iron were adjusted for baseline levels. In the Dialysate-Fe group, the average weekly dose of intravenous iron significantly declined from an average of 68.7 mg in month '0' to 8.9 in month '6' (p<0.002). The average weekly dose of intravenous iron in IV-Fe group did not change significantly from 68.7 mg in the baseline period to 56.2 mg in the 6th month (p>0.7). Furthermore, in month '6', only 2 out of the 10 patients receiving dialysate iron required additional intravenous iron supplements.

3. Transfer of Iron from the Dialysate to the Blood Compartment

Figure 7:
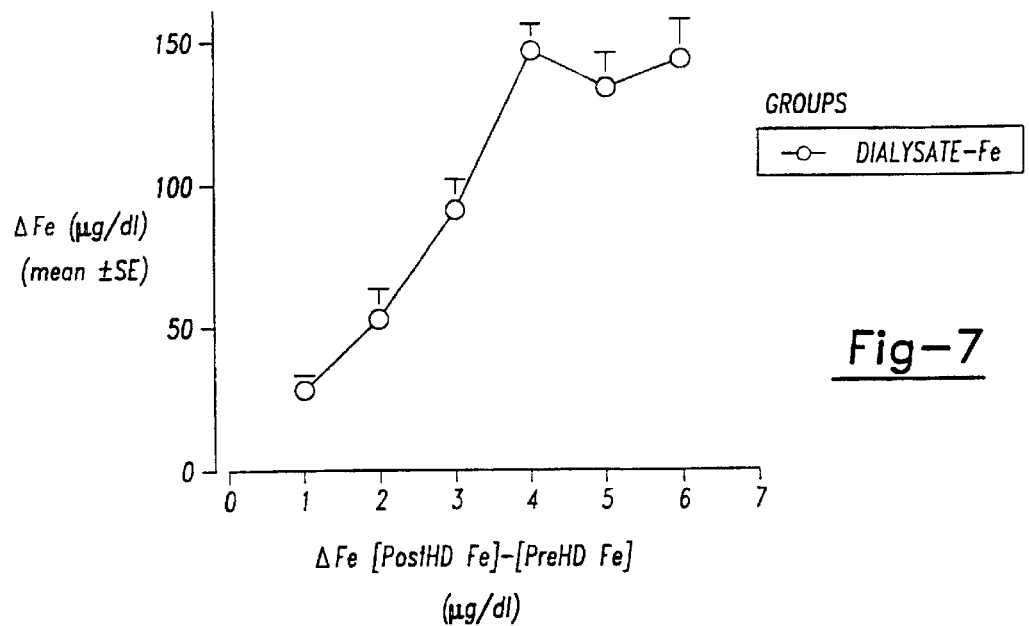
FIG. 7 is a graph of the group increment in average serum iron with dialysis over the study period.
Figure 10:
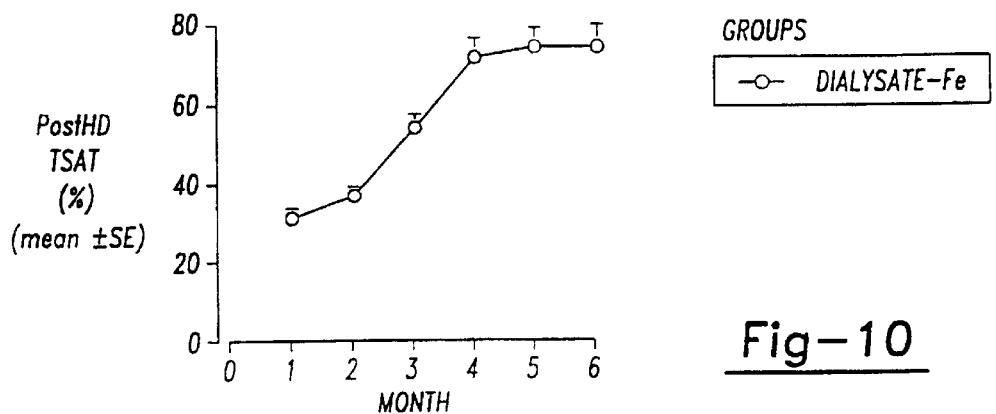
FIG. 10 is a graph of the group postdialysis transferrin saturation (TSAT) average over the study period.
Figure 11:
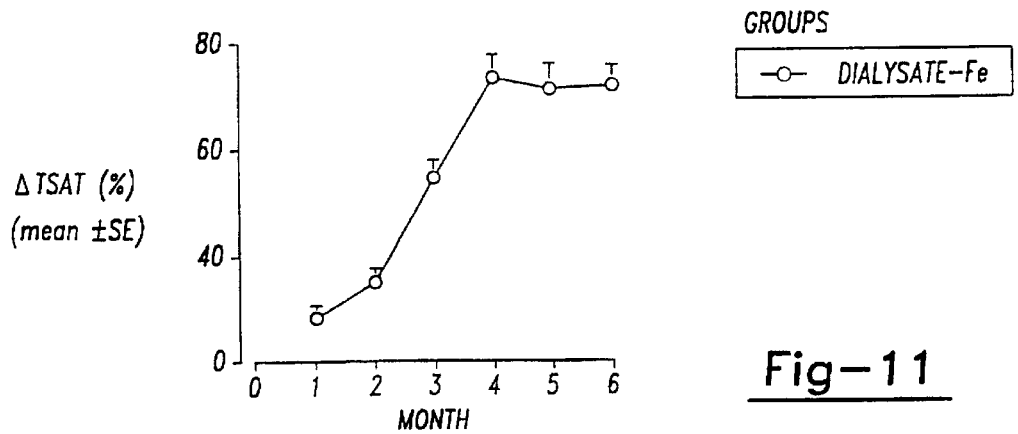
FIG. 11 is a graph of the group average change in transferrin saturation (TSAT) during dialysis over the study period.
Figure 12:
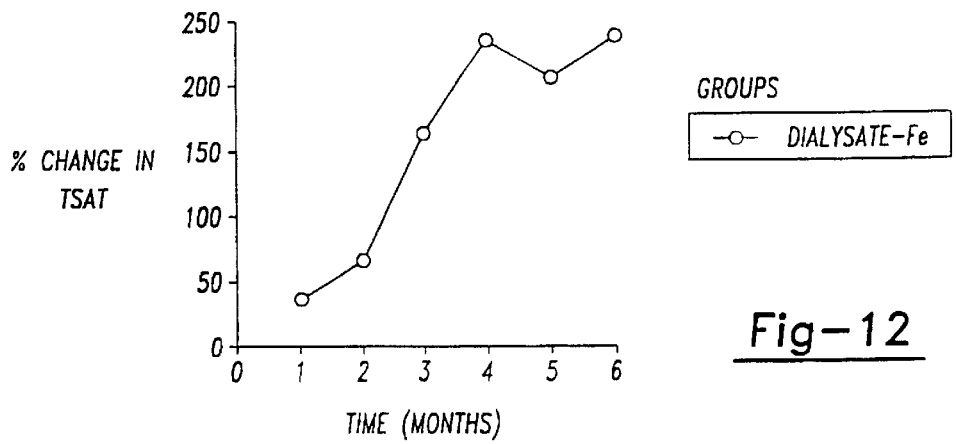
FIG. 12 is a graph of the group average percentage change in mean transferrin saturation (TSAT) with dialysis over the study period.

The decrease in intravenous iron requirement in the Dialysate-Fe group was accompanied by a dose dependent transfer of iron from dialysate to the blood compartment as reflected by the increment in serum iron with dialysis (FIG. 7). With addition of iron to the dialysate there was a dose dependent increase in post-dialysis TSAT (mean±SD) to 31.7±6.8% on 2 µg/dl, 37.0±8.3% on 4 µg/dl, 54.7±9.9% on 8 µg/dl and 71.75±13.4% on 12 µg/dl (FIG. 10). Hence the increment in TSAT and percentage change in TSAT during dialysis were dependent on the concentration of dialysate iron (FIGS. 11 and 12).

4. Total Iron Binding Capacity

Figure 8:
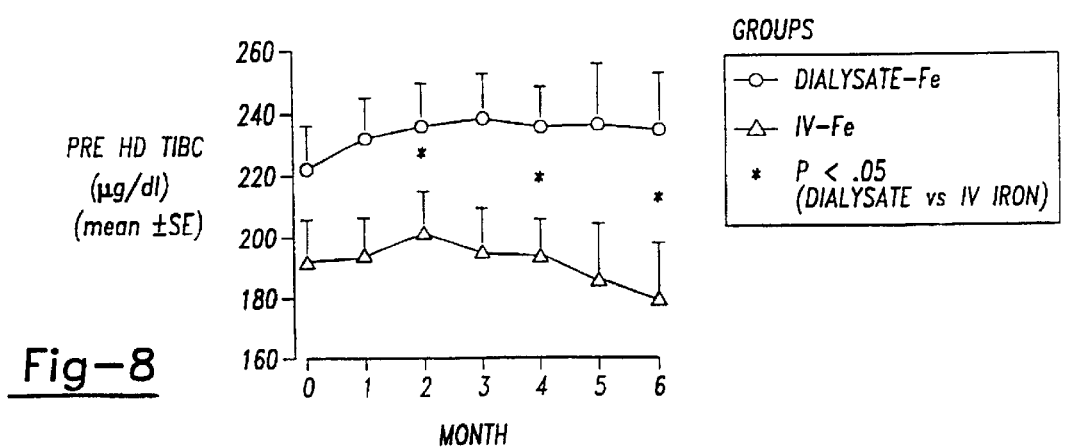
FIG. 8 is a graph of the group predialysis total iron binding capacity average over the study period.

The baseline total iron binding capacity (TIBC, mean±S.D.) was 222.3±43.8 µg/dl in Dialysate-Fe group and 192.7±48.1 µg/dl in IV-Fe group, and the differences between the two groups was not significant (p>0.14) (FIG. 8). TIBC at 6 months, adjusted for the baseline values, was significantly higher in the Dialysis-Fe group (p<0.05). Circulating transferrin increases in the presence of iron deficiency. However, based on reticulocyte hemoglobin and serum iron parameters, there was no difference in the iron status between the two groups. Transferrin can be suppressed in patients with reticuloendothelial block and anemic of chronic disease. However, nutritional parameters, serum ferritin and reticulocyte hemoglobins in the two groups do not suggest that patients in the IV-Fe group were sicker or had a reticuloendothelial block in iron release. Therefore, the reason for a difference in TIBC between the two groups towards the end of the study remains unclear.

5. Tissue Stores of Iron

Serum ferritin is a marker for the tissue stores of iron. To ensure adequate supply of iron to the bone marrow, the recommended target range for serum ferritin in the dialysis patients receiving erythropoietin therapy is 100–500 µg/L. The baseline serum ferritin was 154±120 µg/L in Dialysate-Fe group and 261±211 µg/L in the IV-Fe group (mean±S.D.), and the difference between the 2 groups was not statistically significant (FIG. 13). There was no significant change in serum ferritin, in either group, during the course of the study. The serum ferritin level in month "6" was 154±120 µg/L in Dialysate-Fe group and 261±211 µg/L in the IV-Fe group (mean±S.D.), and the difference between the 2 groups was not statistically significant (FIG. 13). These results demonstrate that infusion of iron with every dialysis session by the dialysate route does not lead to excessive tissue accumulation of iron or iron overload.

6. Safety Results

No adverse effects secondary to the use of dialysate iron therapy were identified. Specifically, monitoring of vital signs, physical symptoms or signs and laboratory parameters did not reveal any evidence of pulmonary, cardiovascular or liver toxicity. None of the patients receiving dialysate iron manifested any allergic or anaphylactic reactions. Dialysate iron did not have any significant effect on serum calcium or phosphate concentrations.

7. Summary and Conclusions

In maintenance hemodialysis patients, over a period of 6 months, dialysate iron therapy is:

(a) safe and does not lead to hypotension or anaphylaxis;

(b) maintains iron balance in approximately 80% of patients without supplemental oral or intravenous iron;

(c) the requirements for intravenous iron may be reduced by about 80%;

(d) maintains hemoglobin without an increase in erythropoietin requirement;

(e) does not lead to iron overload.

EXAMPLE 3

Peritoneal Dialysis with Solutions Containing Ferric Pyrophosphate for Iron Supplementation in Rabbits Peritoneal dialysis (PD) patients are less prone to iron deficiency than hemodialysis patients. However, PD patients lose blood through the gastrointestinal tract and from phlebotomy for laboratory tests. Furthermore, iron utilization is increased in dialysis patients treated with erythropoietin. Consequently, iron deficiency is common in PD patients. Iron supplementation in PD patients is commonly accomplished by the oral route, since intravenous access is not as readily available in PD patients. In fact, peripheral intravenous access may be impossible to obtain in some patients when the veins have been thrombosed by venesection or cannulation. In this situation, intravenous iron infusion would necessitate cannulation of a central vein. Both oral and intravenous routes of iron deficiency are associated with numerous side effects. Therefore, addition of iron compounds to peritoneal dialysis solutions merits investigation as an alternative means of iron delivery because of the ease of administration. This method would also be expected to provide a slow continuous and more physiological replacement of ongoing iron losses.

Intraperitoneal administration of iron has been tested in rats with disappointing results. Peritoneal dialysis with a dialysate solution containing 984 µg/dl iron (as colloidal iron dextran) failed to increase the. serum iron concentrate after 6 hours (Suzuki, et al., 1995). Higher concentrations of iron dextran, though successful in increasing serum iron concentration, are toxic to the peritoneum. Iron dextran induces an inflammatory response leading to peritoneal adhesions and fibrosis, and a brownish pigmentation of the peritoneal membrane from deposition of iron. Therefore, colloidal iron dextran is not suitable for administration by the intraperitoneal route. Other colloidal iron compounds are likely to have a similar toxic effect on the peritoneum. A soluble iron salt, ferric chloride, had been tested previously by the same group (Suzuki, et al., 1994). In this study, despite a dialysate iron concentration of 400 $\mu$g/dl (as ferric chloride), there was no change in the serum iron concentration after 6 hours of peritoneal dialysis (Suzuki, et al. 1994).

Results of a Phase I/II trial of iron delivery by the dialysate route in maintenance hemodialysis patients suggest that this is safe, effective and well tolerated. Therefore, addition of soluble ferric pyrophosphate to the peritoneal dialysis solutions was tested as a potential treatment for iron deficiency, in a rabbit model of acute peritoneal dialysis.

A. Materials and Methods

New Zealand white rabbits (n=10) on a standard rabbit diet containing 16 $\mu$g iron per kg and weighing 2.5–3.5 kg were obtained. Control rabbits (n=3) continued to receive the standard diet. Seven rabbits were switched to an iron deficient (20–25 parts per million elemental iron) diet to produce a state of iron deficiency (iron-deficient group).

On day 1, blood was drawn from the central artery of the ear, using a 22 g butterfly needle. Whole blood hemoglobin, serum iron and total iron binding capacity (TIBC) were estimated. A total of 10 ml blood was drawn from control rabbits and 20 ml from rabbits on iron deficient diet. More blood was drawn from rabbits on iron deficient diet, to exacerbate iron deficiency. On days 7 and 14, another 8–10 ml blood was drawn from all ten rabbits for hemoglobin and iron studies.

Peritoneal dialysis was performed only in the Iron deficient group. The volume of peritoneal dialysate per exchange was about 210 ml (70 ml/kg body weight) and the dialysis was performed only on days 14, 21, and 28.

B. Preparation of a Peritoneal Dialysis Solution Containing Ferric Pyrophosphate The dialysate was prepared by adding a sterile filtered ferric pyrophosphate solution to a 2 liter bag of peritoneal dialysis solution (4.25% Dianeal®). The iron concentration in the final dialysate was 500 $\mu$g/dl.

C. Procedures and Data Analysis

Rabbits were sedated using a subcutaneous injection of 2 mg/kg acepromazine and 0.2 mg/kg butorphanol, and restrained on a board in a supine position. Blood was drawn for hemoglobin and iron studies. The skin over the abdominal wall was shaved, disinfected with betadine and anesthetized by instillation of 1% lidocaine. A 18 g angiocath was advanced into the peritoneal cavity for infusion of dialysis solution. After 210 ml dialysate had been infused from a 2 liter bag, infusion was stopped, the angiocath was removed and the rabbit was returned to its cage.

Blood samples were drawn for iron studies, 30 and 120 minutes after starting dialysis. After the 120 minute blood draw, the rabbit was sedated as described previously and restrained in a prone upright position. A 18 g angiocath was reinserted into the peritoneal cavity and the dialysate was drained by gravity. After the dialysate had stopped draining, the angiocath was removed and the rabbit was returned to its cage.

Serum iron level was estimated by a calorimetric method, after separating iron from transferrin and then converting it into divalent iron. The total iron binding capacity (TIBC) was measured using the modified method of Goodwin.

The serum iron levels and transferrin saturation were compared at 0, 30 and 120 minutes using the Wilcoxon signed rank test. A P value of less than 0.05 was considered statistically significant. The study protocol was approved by the Institutional Review Board for the care of animal rights.

D. Results

Figure 16:
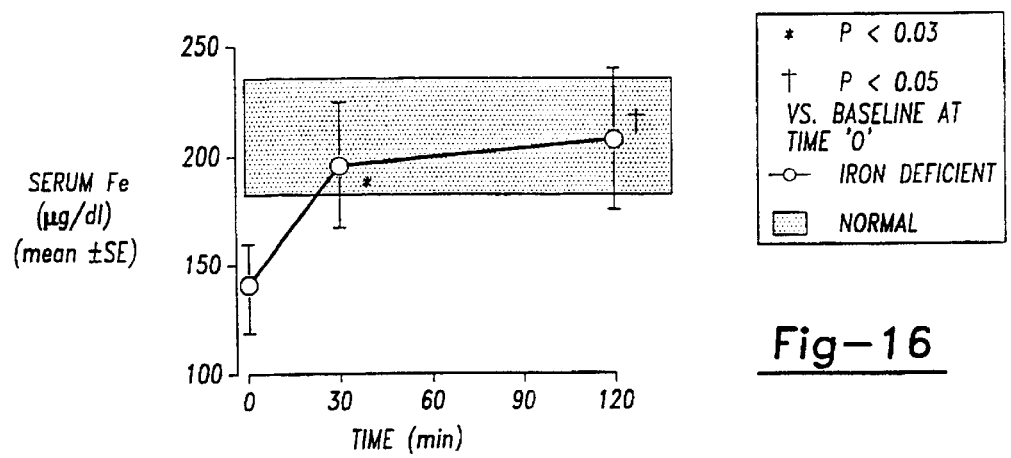
FIG. 16 is a graph showing the serum iron in rabbits undergoing acute peritoneal dialysis with a dialysis solution that contains ferric pyrophosphate.
Figure 17:
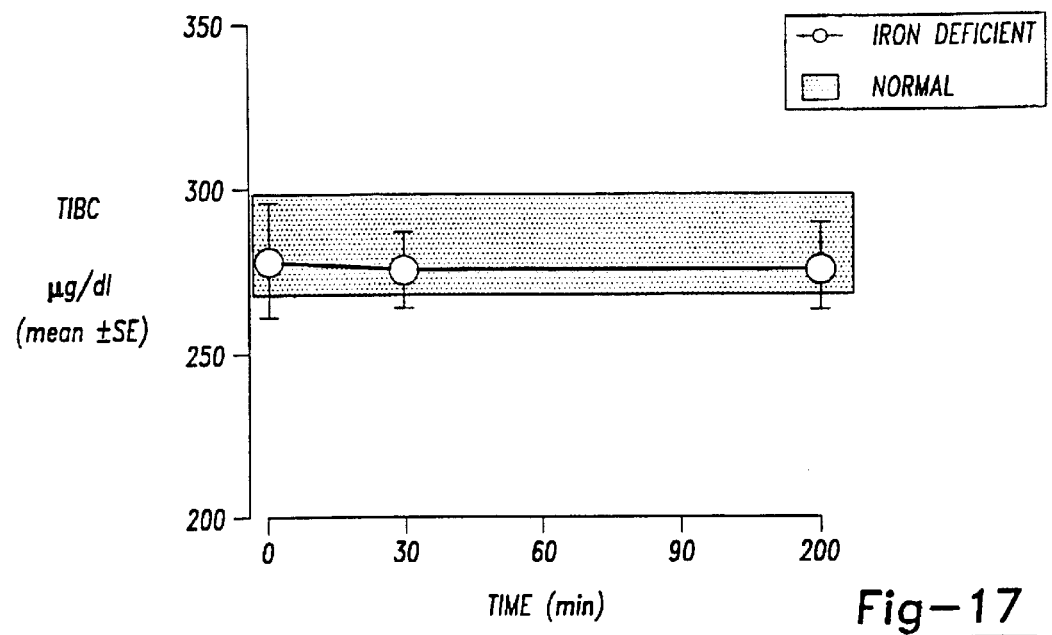
FIG. 17 is a graph showing total iron binding capacity (TIBC) in rabbits during peritoneal dialysis.
Figure 18:
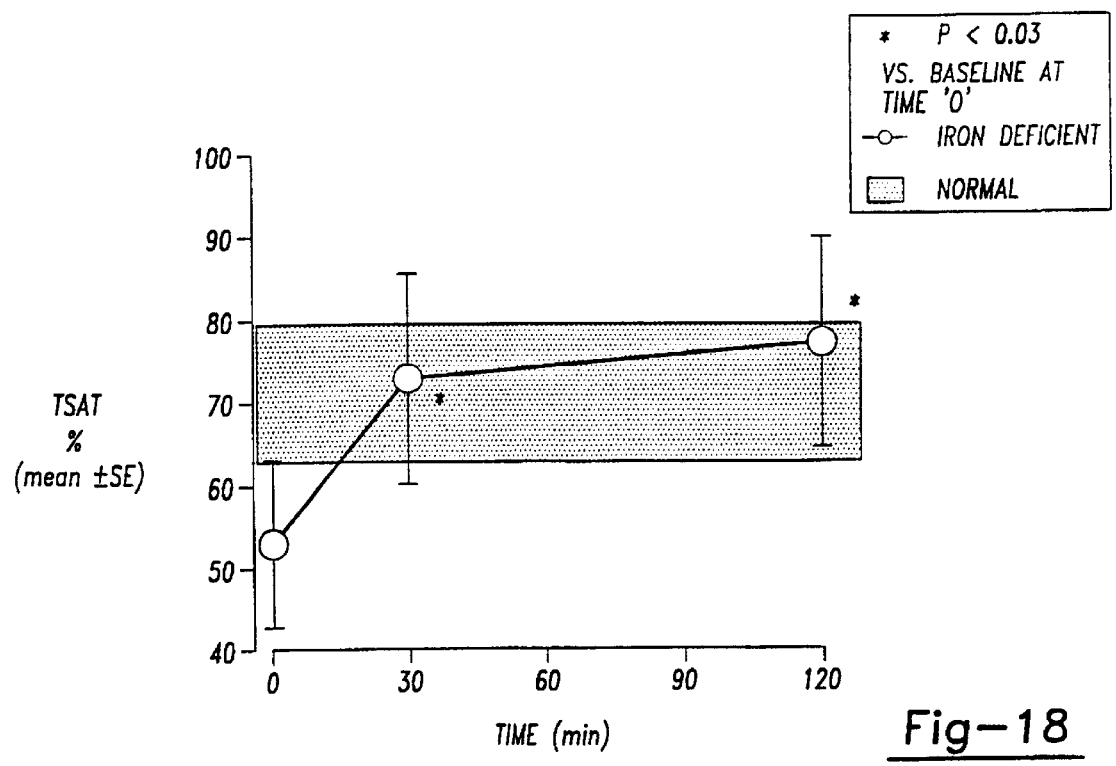
FIG. 18 is a graph showing the transferrin saturation (serum Fe/TIBC, %) in rabbits undergoing acute peritoneal dialysis with a dialysis solution that contains ferric pyrophosphate.

A significant decrease in baseline serum iron and transferrin saturation was observed in rabbits that were fed an iron deficient diet, compared with the control group (FIGS. 16 and 18). The hatched rectangles in FIGS. 16–18 represent mean±1 S.D values in the control group.

Iron deficient rabbits were dialyzed with a dialysis solution containing ferric pyrophosphate. Peritoneal exchanges were performed on study days 14, 21 and 28. Similar results were seen in all experiments. Results of the experimental dialysis performed on day 21 are described below.

During the course of peritoneal dialysis, a significant increase in serum Fe and transferrin saturation was evident at 30 minutes (P<0.03). Consequently, the mean serum iron and transferrin saturation increased into the normal range, in this group of iron deficient rabbits within 30 min. of starting dialysis. Peritoneal dialysis was continued for a total period of 2 hours. The significant increase in serum levels of iron and transferrin saturation was sustained for the duration of the experiment.

On day 28, after the final dialysis had been completed, all the animals were euthanized and specimens of the visceral and parietal peritoneum were obtained for histologic examination. No macroscopic or microscopic changes were observed and no apparent iron deposition was detected by Prussian blue staining. Therefore, ferric pyrophosphate does not have any acute toxic effects on the peritoneal membrane.

E. Summary

The above is an example of (1) a novel formulation for iron supplementation in peritoneal dialysis; and (2) the first demonstration that addition of soluble iron salts to the peritoneal dialysate is a feasible method of iron delivery.

EXAMPLE 4

Administration of Soluble Iron by Parenteral Routes

Dialysis involves diffuse transport of molecules across a semipermeable membrane. For a molecule that is present on both sides of the membrane, there is transport in both directions but the net transport occurs along the concentration gradient. Free plasma iron is highly toxic and therefore, almost all circulating iron is bound to proteins and plasma concentration of free iron is negligible. Consequently, during dialysis there is no transfer of iron from the blood to the dialysate compartment. In fact, when ferric pyrophosphate is added to the dialysate, there is a one way transfer of iron to the blood compartment during dialysis. This resembles parenteral delivery by routes such as intravenous, intramuscular, subcutaneous, or transdermal. Therefore it is possible to administer ferric pyrophosphate parenterally by these routes, both in dialysis and non-dialysis patients.

In the clinical trial of ferric pyrophosphate in hemodialysis patients, the average increment in serum iron concentration during a 3–4 hour dialysis session was about 140 $\mu$g/dl. Assuming a plasma volume of 3.5 liters, it can be estimated that the increment in circulating iron bound to transferrin was about 5.25 mg per dialysis session. The extravascular space contains about as much transferrin as the intravascular space, and there is a free exchange of iron in between the two pools of transferrin. Therefore, it can be estimated that a total of about 10.5 mg iron (or about 105 mg ferric pyrophosphate) was transferred to the patient during a dialysis session. This indicates that in dialysis or non-dialysis patients, it is possible to infuse a sterile solution of ferric pyrophosphate at a rate of about 40 mg per hour. Intermittent or continuous intravenous infusion may be administered if an intravenous access is available. In non-hemodialysis patients, intravenous access may be difficult, and it may be possible to deliver ferric pyrophosphate by subcutaneous implants, or by a transdermal delivery system.

In summary, ferric pyrophosphate may be delivered by the dialysis route in hemodialysis (example 1 and 2) peritoneal route, inperitoneal dialysis patients (example 3), or intravenous/subcutaneous/intramuscular/transdermal routes in dialysis or non-dialysis patients (example 4).

EXAMPLE 5

Regulation of Hematologic Parameters in Dialysis Patient by Modification of Dialysis Solutions The results of the clinical study in Example 2, demonstrate a novel method of hematologic manipulation during dialysis by modification of dialysate solutions, as exemplified by the maintenance of hematological parameters in a narrow target range by regular delivery of iron by dialysis.

The oral or intravenous methods of iron delivery are often unable to maintain optimal iron balance in dialysis patients. With continued loss of iron and increased iron consumption during erythropoietin therapy, iron deficiency develops. As hemoglobin/hematocrit declines, the dose of erythropoietin is often increased and iron administered intravenously, to maintain hemoglobin/hematocrit in the target range. Consequently, hemoglobin/hematocrit rise and this phenomenon has been termed "hematocrit or hemoglobin cycling".

Administration of ferric pyrophosphate by the dialysate route during every dialysis session is able to maintain levels of iron, transferrin saturation (FIGS. 6 and 9) and hemoglobin (FIG. 4) in a narrow target range. Therefore, dialysate delivery of ferric pyrophosphate abolishes hematocrit cycling (FIG. 4), by maintaining an optimal iron delivery to the erythron (FIG. 5). This is also the first example of hematological manipulation by modification of dialysate.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

References

Allegra V, Mengozzi G, Vasile A. Iron deficiency in maintenance hemodialysis patients: assessment of diagnosis criteria and of three different iron treatments. *Nephron* 1991;57:175–182.

Byrd T F, Horwitz M A. Lactoferrin inhibits or promotes Legionella Pneumophilia intracellular multiplication in nonactivated and interferon gamma-activated human monocytes depending upon its degree of iron saturation. Iron-lactoferrin and nonphysiologic iron chelates reverse monocyte activation against Legionella Pneumophilia. *J Clin Invest* 1991;88(4):1103–1112.

Carver F G, Frieden E. Factors affecting the adenosine triphosphate induced release of iron from transferrin. *Biochemistry* 1987;17(1):167–172.

Collins A, Ebben J, Ma J. Frequent IV iron dosing is associated with higher infectious deaths. *J Am Soc Nephrol* 1997;8:190A.

Cox J S G, King R E, Reynolds G F. Valency investigations or iron dextran ('Imferon'). *Nature* 1965,207:1202–1203.

Erslev A J. Erythropoietin. *N Engl J Med* 1991;324(19):1339–1344.

Eschbach J W, Cook J D, Scribner B H, Finch C A. Iron balance in hemodialysis patients. *Ann Intern Med* 1977;87:710–713.

Hamstra R, Block M, Schocket A. Intravenous iron dextran in clinical medicine. *JAMA* 1980;243:1726–1731.

Harken A H, Simson M B, Hasilgrove J. Early ischemia after complete coronary ligation in the rabbit, dog, pig and monkey. *Am J Physiol* 1981;241:H202.

Heath C W, Strauss M B, Castle W B. Quantitative aspects of iron deficiency in hypochromic anemia. *J Clin Invest* 1932;11:1293.

Horl W. Consensus Statement: How to diagnose and correct iron deficiency during r-huErythropoietin therapy—a consensus rerythropoietinrt. *Nephrol Dial Transplant* 1996;11:246–250.

Ifudu O, Feldman J. Friedman E A. The intensity of hemodialysis and the response to erythropoietin in patients with end stage renal disease. *N Engl J Med* 1996;334:420–425.

Jacobs K, Shoemaker C, Rudersdorf R. Isolation and characterization of genomic and cDNA clones of human erythropoietin. *Nature* 1985;313:806–810.

Javaid N, Haschke F, Pietschnig B, et al. Interactions between infections, malnutrition and iron nutritional status in Pakistani infants. A longitudinal study. *Acta Paediatrica Scandinavica—Supplement* 1991;374:141–50.

Kleiner N J, Van Wyck, D B, Kaupke C J, Kirlin L F. The role of iron and other factors in patients unresponsive to erythropoietin therapy. *Seminars in Dialysis* 1995;8(1):29–34.

Konopka K, Mareschal J C, Crichton R R. Iron transfer from transferrin to ferritin mediated by polyphosphate compounds. *Biochim Biophys Acta* 1981;677:417–423.

Konopka K, Mareschal J C, Crichton R R. Iron transfer from transferrin to ferritin mediated by pyrophosphate. *Biochem Biophys Res Commun* 1980;96(3):1408–1413.

Kumpf V, Hollanf E. Parenteral iron dextran therapy. *DICP Ann Pharmacother* 1990;24:162–166.

Levin N A. The impact of erythropoietinetin alfa: quality of life and hematocrit level. *Am J Kid Dis* 1992;XX(Suppl 1 (July)):16–20.

MacDougall I, Hutton R, Cavill I, Coles G, Williams J. Poor response to the treatment of renal anaemia with erythropoietin corrected by iron given intravenously. *Br Med J* 1989;299:157–158.

Maurer A H, Knight L C, Siegel J A, Elfenbein I B, Adler L P. Paramagnetic pyrophosphate. Preliminary studies on magnetic resonance contrast enhancement of acute myocardial infarction. *Investigative Radiology* 1990;25(2):153–63.

Morgan E H. Studies on the mechanism of iron release from transferrin. *Biochim Biophys Acta* 1979;580(2):312–326.

Morgan E H. Iron exchange between transferrin molecules mediated by phosphate compounds and other cell metabolites. *Biochim Biophys Acta* 1977;499(1):169–177.

Nilsen T, Romslo I. Pyrophosphate as a ligand for delivery of iron to isolated rat-liver mitochondria. *Biochim Biophys Acta* 1984;766(1):233–239.

Park S E, Twardowski Z T, Moore H L, Khanna R, Nolph K D. Chronic injection of iron dextran into the peritoneal cavity of rats [Abstract]. *Peritoneal Dialysis International*. 1997;17(Suppl. 1):31.

Pascual J, Teruel J L, Liano F, Sureda A, Ortuno J. Intravenous Fe-gluconate-Na for the iron-deficient patients on hemodialysis. *Nephron* 1992;60:121.

Pollack S, Weaver J. Guinea pig and human red cell hemolysates release iron from transferrin. *J Lab Clin Med* 1985;105(5):629–634.

Pollack S, Vanderhoff G, Lasky F. Iron removal from transferrin. An experimental study. *Biochim Biophys Acta* 1977;497(2):481–487.

Schaeffer R, Schaefer L. The hypochromic red cell: A new parameter for monitoring or iron supplementation during r-huErythropoietin therapy. *J Perinat Med* 1995;23:83–88.

Schaeffer R, Schaefer L. Management of iron substitution therapy during r-HuErythropoietin therapy in chronic renal failure patients. *Erythropoiesis* 1992;3:71–75.

Sepandj F, Jindal K, West M, Hirsch D., Economic appraisal of maintenance parenteral iron administration in treatment of anaemia in chronic haemodialysis patients. *Nephrol. Dial. Transplant.* 1996;11:319–322.

Sillen L G, Martell A E. Stability constants of metal-ion complexes. The Chemical Society, London, 1964.

Suzuki K, Twardowski Z T, Nolph K D, Khanna R, Moore H L., Absorption of Iron Dextran from the Peritoneal Cavity of Rats. *Advances in Peritoneal Dialysis* 1995; 11:57–59.

Suzuki K, Twardowski Z T, Nolph K D, Khanna R, Moore H L. Absorption of iron from the peritoneal cavity of rats. *Advances in Peritoneal Dialysis*. 1994;10:42–43.

Van Wyck D B, Stivelman J, Ruiz J, Kirlin L, Katz M, Ogden D. Iron status in patients receiving erythropoietin for dialysis-associated anemia. *Kidney Int* 1989;35:712–716.

Weinberg E. Iron withholding: a defense against infection and neoplasia. *Physiol Rev* 1984;64:65–102.

What is claimed is:

1. A method for treating iron deficiency comprising parenterally administering to a patient in need of such treatment an effective amount of ferric pyrophosphate, so that bioavailable iron is safely and effectively administered.

2. A method according to claim 1 wherein the route of administration is selected from the group consisting of subcutaneous, intramuscular, transdermal or intravenous administration.

3. A method according to claim 2 wherein the route is intravenous administration.

4. A method according to claim 2 wherein ferric pyrophosphate is administered to the patient at a rate of about 40 mg per hour.

* * * * *

UNITED STATES PATENT AND TRADEMARK OFFICE
CERTIFICATE OF CORRECTION

PATENT NO. : 6,779,468 B1
DATED : August 24, 2004
INVENTOR(S) : Ajay Gupta

It is certified that error appears in the above-identified patent and that said Letters Patent is hereby corrected as shown below:

Column 18,
Line 45, "diffuse" should read -- diffusive --

Signed and Sealed this

Fourteenth Day of December, 2004

JON W. DUDAS
*Director of the United States Patent and Trademark Office*